(12) United States Patent (10) Patent No.: US 8,901,074 B2
Frenkel et al. (45) Date of Patent: Dec. 2, 2014

(54) METHODS OF TREATING AUTOIMMUNE DISEASES OF THE CENTRAL NERVOUS SYSTEM (CNS) AND NEURODEGENERATIVE DISEASES

(75) Inventors: Dan Frenkel, Rechovot (IL); Hilit Levy, Kadima (IL); Nofit Borenstein, Ramat-Gan (IL); Dorit Farfara, Rehovot (IL); Dorit Trudler, Ramat-HaSharon (IL)

(73) Assignee: Ramot at Tel-Aviv University, Tel-Aviv (IL)

( * ) Notice: Subject to any disclaimer, the term of this patent is extended or adjusted under 35 U.S.C. 154(b) by 0 days.

(21) Appl. No.: 13/813,969

(22) PCT Filed: Aug. 4, 2011

(86) PCT No.: PCT/IL2011/000638
 § 371 (c)(1),
 (2), (4) Date: Feb. 4, 2013

(87) PCT Pub. No.: WO2012/017439
 PCT Pub. Date: Feb. 9, 2012

(65) Prior Publication Data
 US 2013/0130976 A1 May 23, 2013

Related U.S. Application Data

(60) Provisional application No. 61/370,481, filed on Aug. 4, 2010, provisional application No. 61/419,896, filed on Dec. 6, 2010.

(51) Int. Cl.
 *C07K 7/06* (2006.01)
 *C07K 14/00* (2006.01)
 *C07K 7/08* (2006.01)
 *A61K 38/10* (2006.01)
 *A61K 47/48* (2006.01)
 *C07K 14/47* (2006.01)
 *A61K 38/17* (2006.01)

(52) U.S. Cl.
 CPC . *C07K 7/06* (2013.01); *A61K 47/48* (2013.01); *A61K 47/48123* (2013.01); *C07K 7/08* (2013.01); *C07K 14/4703* (2013.01); *A61K 38/1709* (2013.01); *C07K 14/001* (2013.01)
 USPC ......................................................... 514/6.7

(58) Field of Classification Search
 CPC .......... C09B 11/04; G02B 5/223; G03F 7/00; G03F 7/0007; G03F 7/027; G03F 7/105
 See application file for complete search history.

(56) References Cited

U.S. PATENT DOCUMENTS 5,824,319 A 10/1998 Vafai
7,108,972 B2 9/2006 Pena et al.
2003/0104981 A1 6/2003 Mandic
2009/0088367 A1 4/2009 Lipton et al.
2009/0143275 A1 6/2009 Pugia et al.
2012/0028894 A1 2/2012 Frenkel et al.

FOREIGN PATENT DOCUMENTS

| CN | 1292798 | 4/2001 |
|---|---|---|
| CN | 1355813 | 6/2002 |
| CN | 101801412 | 8/2010 |
| WO | WO 99/35169 | 7/1999 |
| WO | WO 00/78805 | 12/2000 |
| WO | WO 03/102016 | 12/2003 |
| WO | WO 2006/128026 | 11/2006 |
| WO | WO 2008/156701 | 12/2008 |
| WO | WO 2010/086867 | 8/2010 |
| WO | WO 2010/123720 | 10/2010 |
| WO | WO 2012/017439 | 2/2012 |

OTHER PUBLICATIONS

Crystal M. Cordes, Nitric Oxide Inhibits Insulin-Degrading Enzyme Activity and Function through S-Nitrosylation, (2009). Public Health Resources. Paper 26.*
Robert G. Bennett, An Insulin-Degrading Enzyme Inhibitor Decreases Amylin Degradation, Increases Amylin-Induced Cytotoxicity, and Increases Amyloid Formation in Insulinoma Cell Cultures, Diabetes, vol. 52, 2003.*
Malcolm A. Leissring, Designed Inhibitors of Insulin-Degrading Enzyme Regulate the Catabolism and Activity of Insulin, PLOS One, 2010, vol. 5, Issue 5.*
Subramaniam Sriram, Experimental Allergic Encephalomyelitits: A misleading Model of Muliple Sclerosis, Ann. Neurol. 2005; 58:939-945.*
Lawrence Steinman, How to Successfully Apply Animal Studies in Experimental Allergic Encephalomyelitis to Research on Multiple Sclerosis, Ann Neurol, 2006;60:12-21.*
Official Action Dated Apr. 15, 2013 From the US Patent and Trademark Office Re. U.S. Appl. No. 13/147,406.
Communication Relating to the Results of the Partial International Search Dated Nov. 30, 2011 From the International Searching Authority Re. Application No. PCT/IL2011/000638.
International Preliminary Report on Patentability Dated Aug. 11, 2011 From the International Bureau of WIPO Re. Application No. PCT/IL2010/000093.
International Preliminary Report on Patentability Dated Feb. 14, 2013 From the International Bureau of WIPO Re. Application No. PCT/IL2011/000638.
International Search Report and the Written Opinion Dated Mar. 13, 2012 From the International Searching Authority Re. Application No. PCT/IL2011/000638.
International Search Report and the Written Opinion Dated Oct. 27, 2010 From the International Searching Authority Re: Application No. PCT/IL2010/000093.
Farris et al. "Insulin-Degrading Enzyme Regulates the Levels of Insulin, Amyloid Beta-Protein, and the Beta-Amyloid Precursor Protein Intracellular Domain In Vivo", Proc. Natl. Acad. Sci. USA, 100(7): 4162-4167, Apr. 1, 2003.

(Continued)

*Primary Examiner* — Julie Ha
*Assistant Examiner* — Erinne Dabkowski

(57) ABSTRACT

An insulin degrading enzyme (IDE) inhibitor for use in the treatment of a disease selected from the group consisting of an autoimmune disease of the central nervous system and a neurodegenerative disease is disclosed.

6 Claims, 11 Drawing Sheets
(2 of 11 Drawing Sheet(s) Filed in Color)

(56) References Cited

OTHER PUBLICATIONS

Ghosh et al. "The Finland—United States Investigation of Non-Insulin-Dependent Diabetes Mellitus Genetics (FUSION) Study. I. An Autosomal Genome Scan for Genes That Predispose to Type 2 Diabetes", American Journal of Human Genetics, 67(5): 1174-1185, Nov. 2000.

Kurochkin et al. "Alzheimer's Beta-Amyloid Peptide Specifically Interacts With and is Degrade by Insulin Degrading Enzyme", FEBS Letters, XP025890466, 345(1): 33-37, May 23, 1994.

Li ct al. "Insulin Degrading Enzyme is a Cellular Receptor Mediating Varicella-Zoster Virus Infection and Cell-to-Cell Spread", Cell, 127(2): 305-316, Oct. 20, 2006.

Meigs et al. "A Genome-Wide Scan for Loci Linked to Plasma Levels of Glucose and HbAlc in a Community-Based Sample of Caucasian Pedigrees. The Framingham Offspring Study", Diabetes, 51(3): 833-840, 2002.

Shen et al. "Structure of Human Insulin-Degrading Enzyme Reveal a New Substrate Recognition Mechanism", Nature, 443: 870-874, Oct. 19, 2006.

Shen et al. "The Mg-Chelatase H Subunit is an Abscisic Acid Receptor", Nature, 443: 823-826, Oct. 19, 2006.

Simkin et al "The Inactivation of Insulin by Tissue Extracts. III. The Effect of Force-Fed Diets on the Insulinase Activity of Rat Liver Extracts", Archives in Biochemistry, 24: 422-428, 1949.

Vinik et al. "Advances in Diabetes for the Millennium: New Treatments for Diabetic Neuropathies", Medscape General Medicine, MedGenMed, 6(3 Suppl.): 13, Aug. 17, 2004.

Wiltshire et al. "Evidence for Linkage of Stature to Chromosome 3p26 in a Large U.K. Family Data Set Ascertained for Type 2 Diabetes ", The American Journal of Human Genetics, 70(2): 543-546, Feb. 2002.

Restriction Official Action Dated Feb. 22, 2013 From the US Patent and Trademark Office Re. U.S. Appl. No. 13/147,406.

Translation of Notification of Office Action Dated Jan. 28, 2013 From the State Intellectual Property Office of the People's Republic of China Re. Application No. 201080014546.2.

Translation of Search Report Dated Jan. 28, 2013 From the State Intellectual Property Office of the People's Republic of China Re. Application No. 201080014546.2.

\* cited by examiner

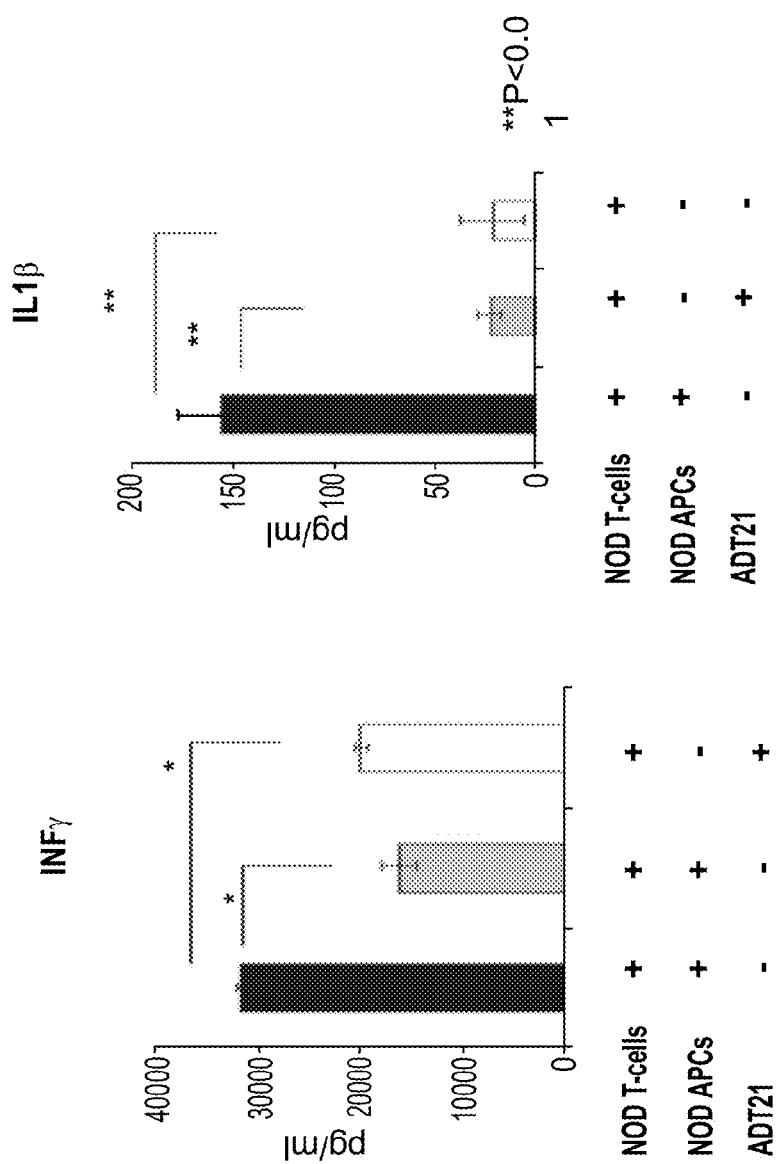

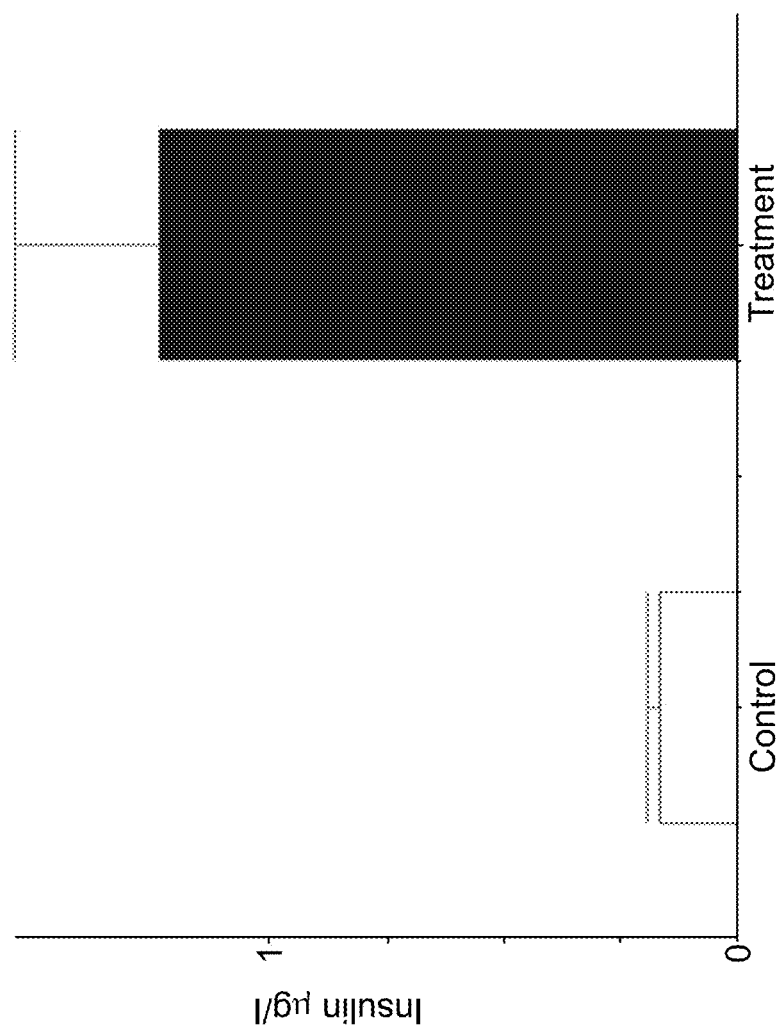

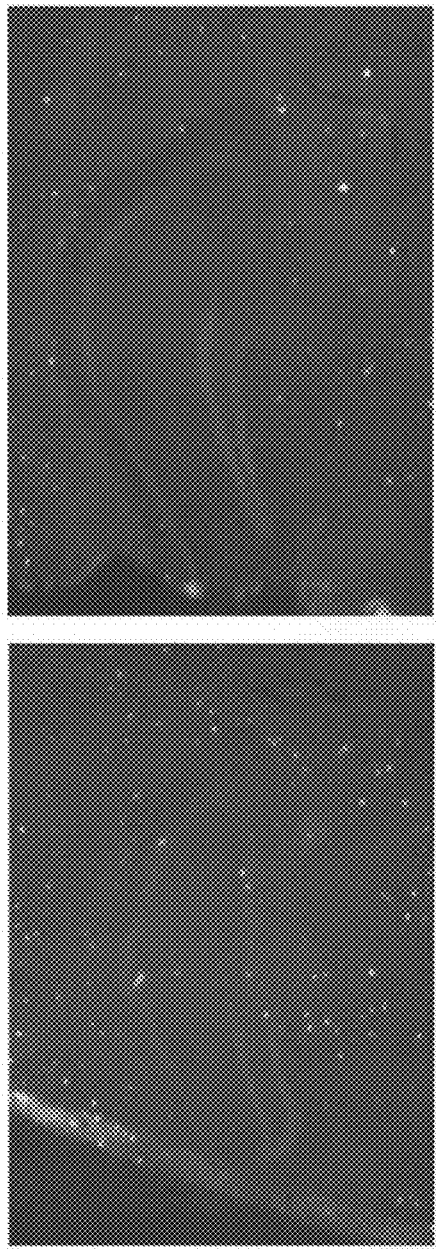
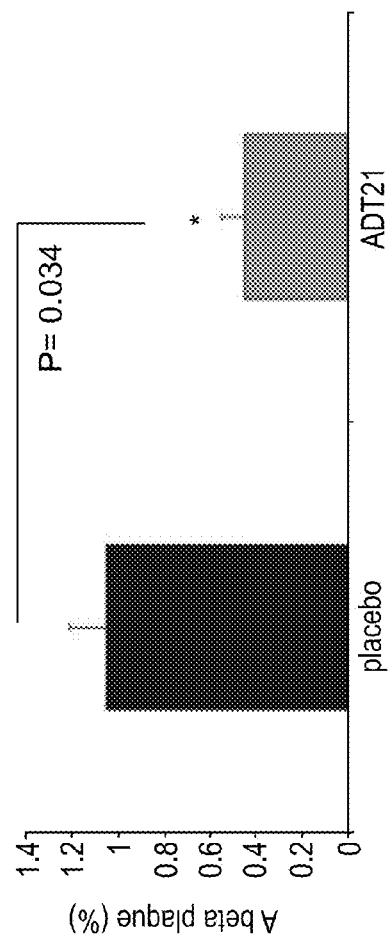
FIG. 10A  FIG. 10B  FIG. 10C

METHODS OF TREATING AUTOIMMUNE DISEASES OF THE CENTRAL NERVOUS SYSTEM (CNS) AND NEURODEGENERATIVE DISEASES

RELATED APPLICATIONS

This application is a National Phase of PCT Patent Application No. PCT/IL2011/000638 having International filing date of Aug. 4, 2011, which claims the benefit of priority under 35 USC §119(e) of U.S. Provisional Patent Applications Nos. 61/370,481 filed on Aug. 4, 2010 and 61/419,896 filed on Dec. 6, 2010. The contents of the above applications are all incorporated by reference as if fully set forth herein in their entirety.

SEQUENCE LISTING STATEMENT

The ASCII file, entitled 55603SequenceListing.txt, created on Jan. 6, 2013, comprising 21,033 bytes, submitted concurrently with the filing of this application is incorporated herein by reference.

FIELD AND BACKGROUND OF THE INVENTION

The present invention, in some embodiments thereof, relates to methods of treating autoimmune diseases of the central nervous system (CNS) and neurodegenerative diseases.

Multiple Sclerosis (MS) is an autoimmune disease of the central nervous system (CNS) characterized by damage to the neuronal myelin sheath, which results in different levels of muscle paralysis that can lead to death. Epidemiological studies show a majority of patients with MS initially develop a relapsing-remitting form of the disease that can develop into secondary-progressive MS. Understanding the mechanisms leading to cumulative neurological disability in multiple sclerosis and further developing effective therapeutic strategies aiming at reduce disease progression is a major goal in MS research.

Innate immunity including dendritic cells, macrophages and activated microglia cells are the key effectors for tissue injury in inflammatory conditions of the CNS. Macrophages do not need activation signals from adaptive immunity to mediate demyelination and tissue injury in the brain. Furthermore, macrophage can promote inflammation through a variety of mechanisms, including the induction of pro-inflammatory cytokines, stimulation of monocyte recruitment and the inhibition of T-cell apoptosis in the lesions.

Since its discovery, Insulin-degrading enzyme (IDE) is considered as an important therapeutic target in diabetes reasoned that inhibitors of IDE would be an ideal anti-diabetic therapy, as they would slow the degradation of insulin.

IDE is an approximately 110 kDa thiol zinc-metalloendopeptidase located in cytosol, peroxisomes, endosomes, and on the cell surface. This enzyme cleaves small proteins of diverse sequences many of which share a propensity to form β-pleated sheet-rich amyloid fibrils, including amyloid β-protein (Aβ), insulin, glucagon, amylin, atrial natriuretic factor and calcitonin [Simkin et al. (1949) Arch Biochem 24: 422-428].

The IDE region of chromosome 10q has been genetically linked to type 2 diabetes mellitus [DM2, Ghosh et al. (2000) Am J Hum Genet. 67:1174-1185; Wiltshire et al. (2002) Am J Hum Genet. 70:543-546] and to elevated fasting glucose levels [Meigs et al. (2002) Diabetes 51:833-840]. Moreover, $IDE^{-/-}$ mice had hyperinsulinemia and glucose intolerance, hallmarks of DM2 [Farris et al. (2003) Proc Natl Acad Sci USA 100:4162-4167]. This model demonstrated that in vivo deficiency of a protease responsible for degrading insulin results in hyperglycemia in response to a glucose load (i.e., glucose intolerance).

Reports have further suggested the role of IDE in degradation of Aβ in Alzheimer's disease [Farris et al., supra]. The elevation of cerebral Aβ in $IDE^{-/-}$ model animals (approximately 10-65%) validated a role for IDE in Aβ proteolysis in vivo, however, there are most likely additional mechanisms of Aβ clearance in the intact brain, especially for Aβ42. Other proteases (e.g., NEP, endothelin-converting enzyme) may participate in Aβ clearance and partially compensate for the lack of IDE function.

IDE is also the cellular receptor mediating varicella-zoster virus (VZV) infection and cell-to-cell spreading [Li et al. (2006) Cell 127:305-316]. Down regulation of IDE by siRNA, or blocking IDE with an antibody, with a soluble IDE protein (extracted from the liver) or with a bacitracin inhibited VZV infection [Li et al., supra]. IDE interacts with glycoprotein E (gE), which is essential for virus infection, through the glycoprotein's extracellular domain, however, IDE does not degrade VZV.

The solved crystal structure of IDE [Shen et al. (2006) Nature 443:870-874] revealed that the amino- and carboxy-terminal domains of IDE (IDE-N and IDE-C, respectively) form a proteolytic chamber containing the zinc-binding active site, just large enough to encapsulate insulin. Extensive contacts between IDE-N and IDE-C keep the degradation chamber of IDE inaccessible to substrates. Repositioning of the IDE domains (shifting IDE-close to its active form IDE-open) enables substrate access to the catalytic cavity. The activity of IDE toward a vast array of physiological substrates can be partially explained by the detailed crystal structure of the enzyme. The structural data revealed that IDE is shaped like a clam shell, consisting of two bowl-shaped halves connected by a flexible hinge, which allows the enzyme to exist in two conformations, closed and open. During catalytic processing of substrates, the enzyme switches from the open structure to the closed configuration and back to the open structure as IDE binds, catalyzes, and then releases its substrate, respectively. The extended hydrogen bonding between the two halves of IDE creates a "latch" that acts to maintain the enzyme in the closed state. Mutations that promote the open conformation have been shown to improve the protease's efficiency in cleaving the substrate by as much as 30- to 40-fold [Shen et al., supra]. As it was suggested that the rate-limiting step may be the speed at which the enzyme can reopen and then clamp down on a new morsel rather than the time it takes to chew something up.

Alzheimer's disease (AD) is the most common type of dementia affecting more than 18 million people worldwide. The main role of beta amyloid (A13) peptide as a to mediator in AD is derived from the fact that it accumulates in the brain several decades before the disease is evident. The accumulation of extracellular and intracellular Aβ can adversely affect distinct molecular and cellular pathways, thereby facilitating tau phosphorylation, aggregation, and an accumulation of neurofibrillary tangle (NFT) formation. Aβ and NFT exhibit synergistic effects that finally lead to an acceleration of neurodegenerative mechanisms involved in metabolism, cellular detoxification, mitochondrial dysfunction, and energy deficiency which results in the formation of neuritic plaques. A number of studies suggest an association between Alzheimer's disease (AD) and diabetes: AD patients show impaired insulin function, which is associated with cognitive deficits. In fact is has been suggested that IDE dysfunction plays a role in Alzheimer's progression.

U.S. Patent Application 20090088367 teaches methods for the prevention or treatment of dementia and other neurological conditions by upregulating the activity of IDE such that insulin competes less efficiently with beta-amyloid protein for the IDE.

Additional Related Art: WO2010/086867

SUMMARY OF THE INVENTION

According to an aspect of some embodiments of the present invention there is provided an insulin degrading enzyme (IDE) inhibitor for use in the treatment of a disease selected from the group consisting of an autoimmune disease of the central nervous system and a neurodegenerative disease.

According to an aspect of some embodiments of the present invention there is provided a method of treating a disease selected from the group consisting of an autoimmune disease of the central nervous system and a neurodegenerative disease, the method comprising administering to a subject in need thereof a therapeutically effective amount of an insulin degrading enzyme (IDE) inhibitor, thereby treating the disease in the subject.

According to some embodiments of the invention, the IDE inhibitor comprises a peptide inhibitor.

According to some embodiments of the invention, the peptide inhibitor comprises an amino acid sequence being no more than 25 amino acids in length, the amino acid sequence comprising at least one aspartate or a homolog thereof, the peptide to having an Insulin-Degrading Enzyme (IDE) inhibitory activity.

According to some embodiments of the invention, the amino acid sequence is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO:13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35 and SEQ ID NO: 36.

According to some embodiments of the invention, the amino acid sequence is as set forth in SEQ ID NO: 6.

According to some embodiments of the invention, the amino acid sequence comprises a moiety which adds flexibility between the at least one aspartate or homolog thereof and an N-terminus sequence of the amino acid sequence.

According to some embodiments of the invention, the moiety which adds flexibility comprises an amino acid sequence.

According to some embodiments of the invention, the amino acid sequence comprises SEQ ID NO: 77.

According to some embodiments of the invention, the N-terminus sequence comprises an IDE binding sequence.

According to some embodiments of the invention, the amino acid sequence comprises an IDE binding sequence.

According to some embodiments of the invention, the IDE binding sequence is selected from the group consisting of SEQ ID NO: 72, SEQ ID NO: 73, SEQ ID NO: 74, SEQ ID NO: 75 and SEQ ID NO: 76.

According to some embodiments of the invention, the at least one aspartate or a homolog thereof comprises two aspartates or homologues thereof.

According to some embodiments of the invention, the two aspartates or homologues thereof are consecutively positioned in the peptide.

According to some embodiments of the invention, the homolog of the aspartate is a structural homologue.

According to some embodiments of the invention, the structural homologue comprises asparagine.

According to some embodiments of the invention, the homolog of the aspartate is a negatively charged amino acid.

According to some embodiments of the invention, the negatively charged amino acid is glutamic acid.

According to some embodiments of the invention, the IDE inhibitor is selected from the group consisting of a nucleic acid agent for silencing IDE expression and a small molecule inhibitor.

According to some embodiments of the invention, the autoimmune disease of the central nervous system is multiple sclerosis.

According to some embodiments of the invention, the neurodegenerative disease is Alzheimer's disease.

According to some embodiments of the invention, the autoimmune disease of the central nervous system is selected from the group consisting of multiple sclerosis, Guillain-Barre syndrome, Lambert-Eaton myasthenic syndrome, Myasthenia gravis, transverse myelitis, progressive multifocal leukoencephalopathy, chronic headache and cerebral palsy.

According to some embodiments of the invention, the subject is a human subject.

According to some embodiments of the invention, the IDE inhibitor is attached to a cell penetrating moiety.

According to some embodiments of the invention, the IDE inhibitor is formulated for passage through the blood brain bather.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-F depict reduction of pro-inflammatory cytokines in IDE−/− mice vs. WT and NOD mice. 10 weeks old C57BL/6 and in IDE−/− mice (n=3-4) were injected with 100

µg of spinal cord lysate, the splenocytes were removed and cultured in the presence of anti-CD3 0.5 µg/ml. The levels of the secreted pro-inflammatory cytokines INF-γ (FIG. 1A) and IL-17 (FIG. 1B) were measured by ELISA; FIGS. 1C-F, 10 weeks old NOD mice, and 8 weeks old C57BL/6 and IDE−/− mice were injected with 250 µg MOG35-55 and 400 µg CFA. Splenocytes were removed and cultured in the presence of 100 µg/ml MOG35-55. The levels of the secreted pro-inflammatory cytokines INF-γ (FIG. 1C), IL-17 (FIG. 1D), TNFα (FIG. 1E) and IL-6 (FIG. 1F) (n=4-7) were measured by ELISA. Results are represented as mean±SEM. *(p<0.05); *(p<0.0005); ***(p<0.0001). Of note, the level of cytokines released from cells obtained from IDE−/− mice was significantly lower as compared to C57BL/6 WT mice, while the level of NOD cytokines was remarkably higher.

Figure 2:
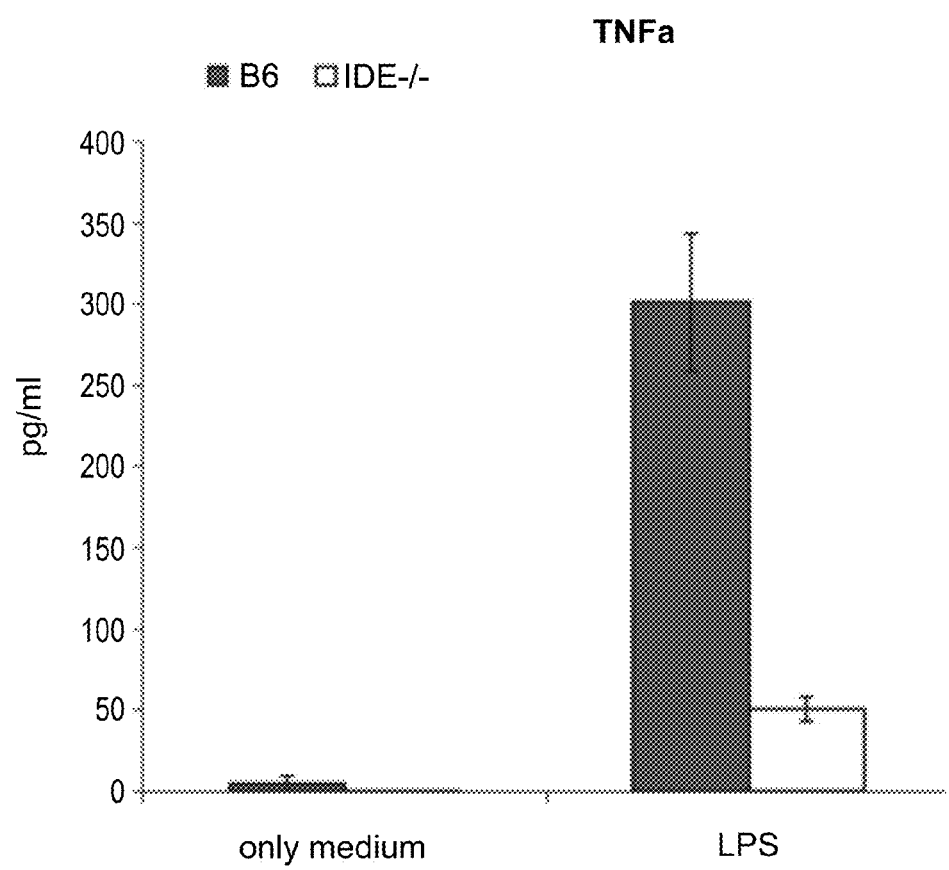

FIG. 2 depicts reduction in release of the pro-inflammatory cytokine TNF-α in IDE−/− mice. Mice splenocytes from WT and IDE−/− were removed and cultured in the present of 0.1 ug/ml LPS (n=3). TNF-α pro-inflammatory cytokines were measured by ELISA. Of note, the level of cytokines released by IDE−/− was significantly lower as compared to C57BL/6. Results are presented as mean±SEM. *(p<0.0002)

Figure 3B:
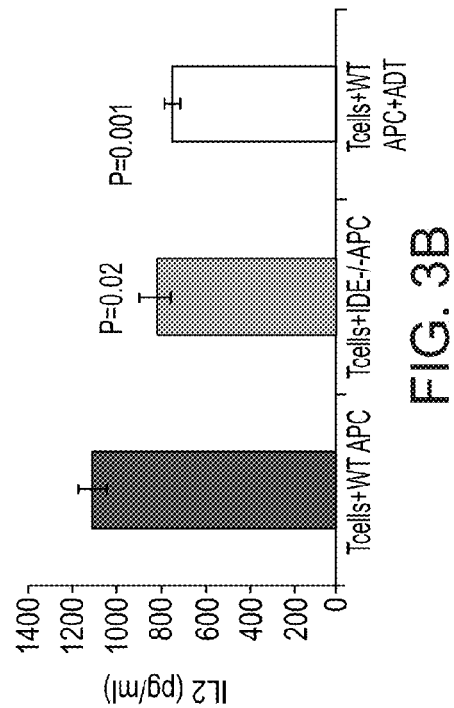
Figure 3A:
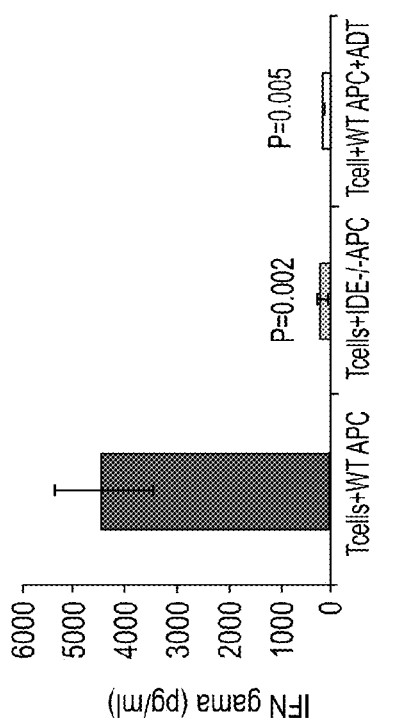
Figure 3C:
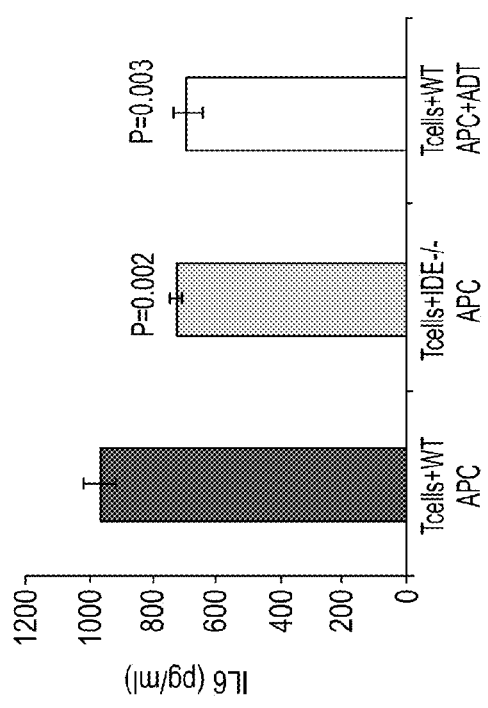

FIGS. 3A-C depict that incubation of CD4+ T-cells in the presence of either an IDE inhibitor or IDE−/− macrophages reduces pro-inflammatory cytokine levels. CD4+ T-cells from C57BL/6 MOG35-55 immunized mice were isolated using magnetic beads and co-cultured with APC from non-immunized mice or together with 100 µg/ml MOG and ADT21. To measure cytokines production, culture supernatants were collected after 48 h for IFN-γ (FIG. 3A) and IL-2 (FIG. 3B) and IL-6 (FIG. 3C). Quantitative ELISA was performed (n=5). Results are presented as mean±SEM.

FIGS. 4A-B depict incubation with the presence of either ADT21 or IDE−/− macrophages reduces levels of the Th1 cytokine IFN-γ and the monocyte cytokine IL-1β. CD4+ T-cells from NOD MOG35-55 immunized mice were isolated using magnetic beads and co-cultured with non-immunized NOD or together with 100 µg/ml MOG and ADT21. To measure cytokines production, culture supernatant was collected after 48 h for IFN-γ (FIG. 4A) and IL-1β (FIG. 4A) and quantitative ELISA was performed. Results are presented as mean±SEM.*(p<0.02); **(p<0.01).

Figures 5A, 5B:
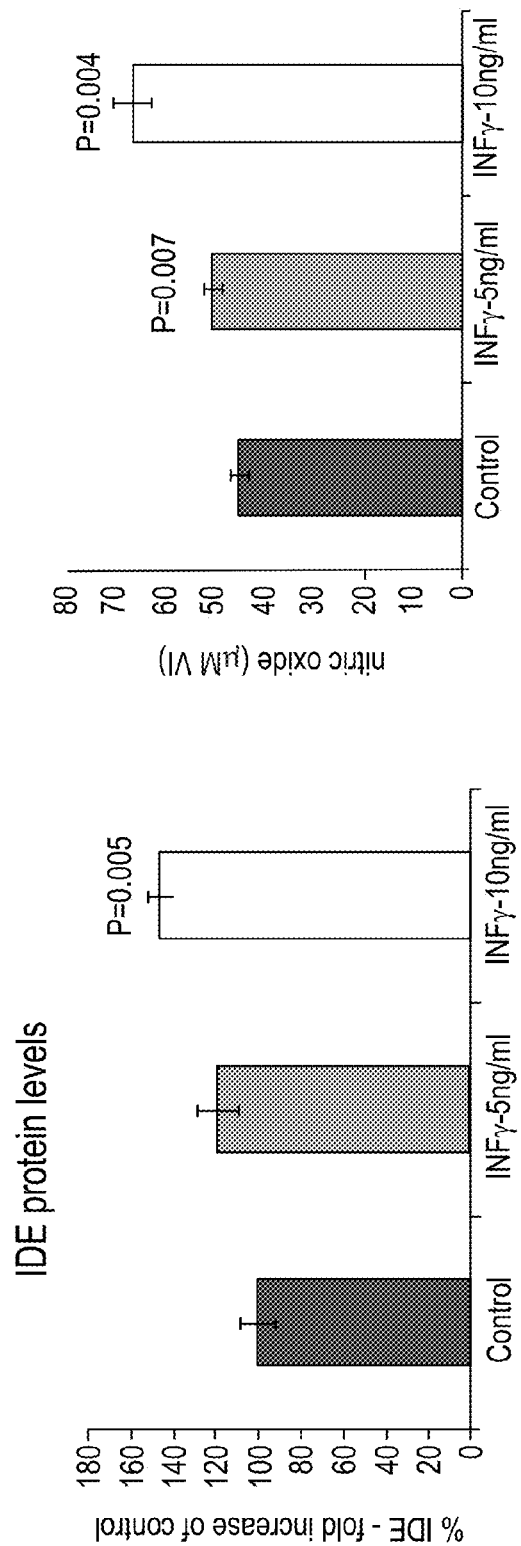
Figure 6A:
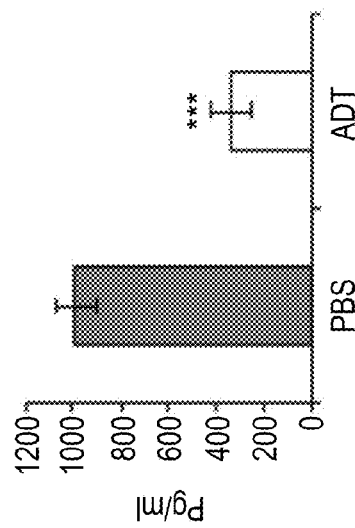
Figure 6B:
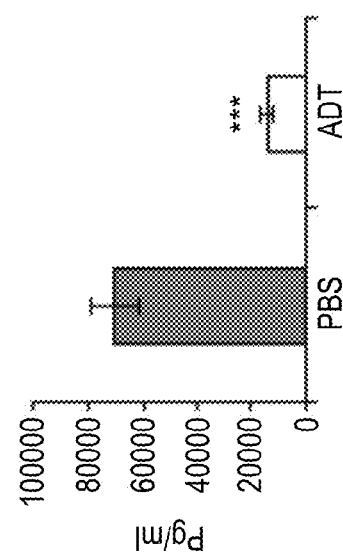
Figure 6C:
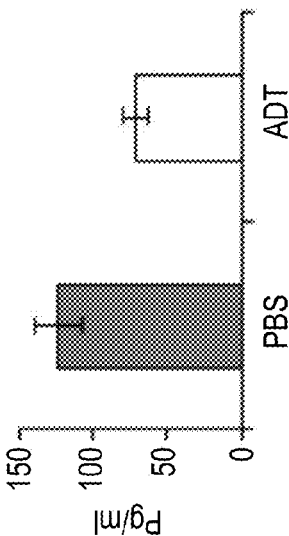
Figure 6D:
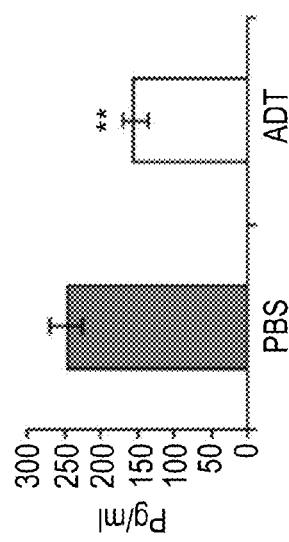

FIGS. 5A-B depict that incubation of macrophages in the presence of IFN-γ increases IDE expression levels on N9 microglia cell line. FIG. 5A, microglia cells were incubated with 5 ng/ml or 10 ng/ml IFN-γ for 24 hrs and the levels of IDE expression were measured using anti-IDE antibody (Abcam) as compared to GAPDH. FIG. 5B, nitrite levels (µM) were measured from cell culture supernatants using the Quantichrom Nitric Oxide assay kit (DINO-250). Results are presented as mean±SEM (n=4).

FIGS. 6A-D depict a reduction in pro-inflammatory cytokine release following administration of IDE−/− inhibitor. EAE induced C57BL/6 (WT) mice (n=4) were administered nasally with 1.07 µg IDE inhibitor, ADT-21, daily. 10 days following EAE induction, the splenocytes were removed and cultured in the presence of MOG35-55. The levels of pro-inflammatory cytokine release were measured after 48 hour incubation using ELISA. Of note, there was a significant reduction in the production of IFN-7 (FIG. 6A) and IL-17 (FIG. 6B); *(p<0.0001); as well as in the production of IL-6 (FIG. 6C)(p<0.005) and TNF-α (FIG. 6D)*(p<0.01); in ADT treated mice compared to non-treated mice. Results are presented as mean±SEM.

Figure 7:
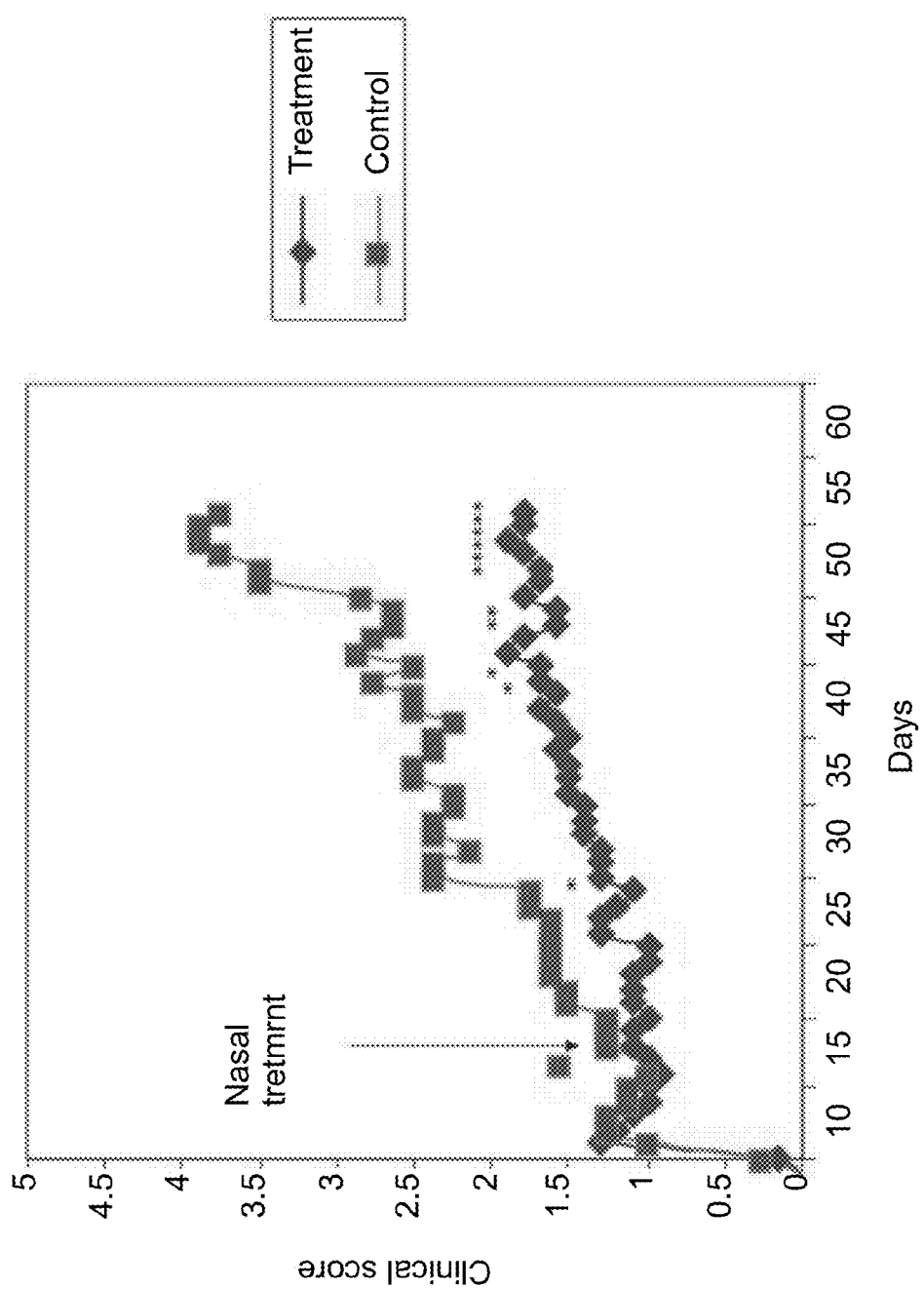

FIG. 7 depict that nasal vaccination with an IDE inhibitor significantly reduces disease progression in MS animal model. EAE was induced in 10 weeks old NOD mice (n=5) and the clinical score was assessed daily for a period of 60 days. Mice began to be treated nasally with IDE inhibitor 18 days after EAE induction, every other day. The clinical score was significantly reduced in the treated mice as compared to PBS treated mice*(p<0.05) (n=4).

Figure 8:
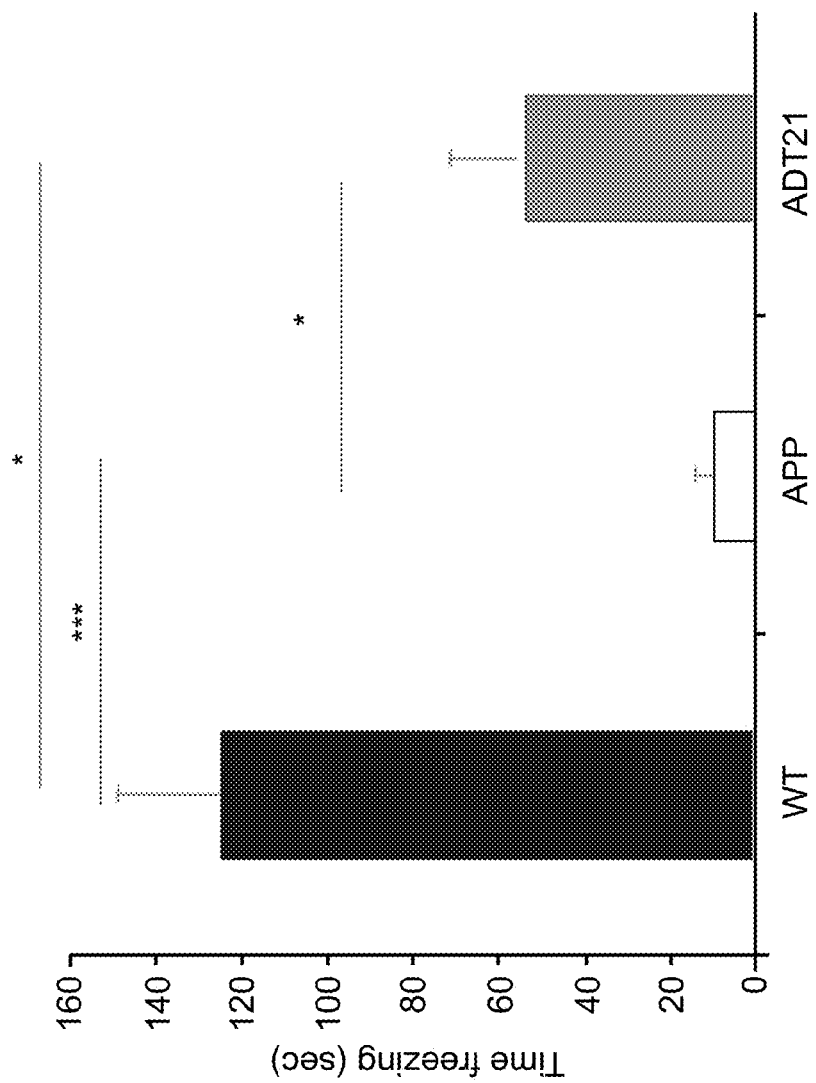

FIG. 8 depicts that ADT21 treatment improves cognitive behavior in APP/PS1 mouse model, as tested in contextual fear conditioning. Time freezing was elevated in 6 months old APP/PS1 mice treated with ADT21 (n=6), as compared to 6 months old to APP/PS1 mice treated with Placebo (PBS, n=4) or untreated (n=10). Results are presented as mean±SEM. *(p<0.05); (p<0.005); *(p<0.0005).

FIG. 9 depicts that ADT21 treatment increases insulin levels in AD Tg mouse model. 2 months APP/PS1 males were nasally treated with ADT21 or placebo, for 4 months every two days (n=5). Mice were sacrificed and their blood was collected. Insulin (ug/L) serum levels were determined using Ultrasensitive mouse Insulin ELISA kit (Mercodia). *p<0.05.

FIGS. 10A-C depict that nasal IDE inhibitor reduces Aβ burden in aggressive Tg mouse model. 2 month old APP/PS1 mice were treated nasally for 4 months, every two days with ADT21 or with placebo (PBS treated mice). The brains were perfused and freshly frozen for 72 hours. 14 µm coronal brain sections were prepared from 6-month-old APP/PS1 mice using cryostat. The slices were then stained at Bregma −1.58 mm with Congo Red staining [Sigma-C6767].

DESCRIPTION OF SPECIFIC EMBODIMENTS OF THE INVENTION

The present invention, in some embodiments thereof, relates to methods of treating autoimmune diseases of the central nervous system (CNS).

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Multiple Sclerosis (MS) is an autoimmune disease of the central nervous system characterized by damage to the neuronal myelin sheath, which results in different levels of muscle paralysis that can lead to neuronal death. Antigen presenting cells (APC) such as macrophage and dendritic cells can promote inflammation through a variety of mechanisms, including the induction of pro-inflammatory cytokines, stimulation of monocyte recruitment and the inhibition of T-cell apoptosis in the lesions. Thus, blockade of APC activation or inhibition of their migration into the CNS can ameliorate clinical MS and tissue injury.

Insulin-degrading enzyme (IDE) is a large zinc-binding protease known to to cleave multiple short polypeptides, and plays an important role in degrading insulin.

The present inventors have recently demonstrated both in cell culture and in autoimmune diabetic animal model, diabetes type I, that IDE inhibitor reduced secretion of pro-inflammatory cytokines such as IL-17 and IFN-gamma, from insulin specific CD4+ T-cell that previously were shown to be involved in the pathogenesis of Type I diabetes.

The present inventors have uncovered that IDE inhibitors down-regulate activation of antigen presenting cells (APC) and CD4+ T cells and down-regulate secretion of pro-inflammatory cytokines from these cells (e.g. IL-1β and IFN-γ, respectively). Indeed, when the present inventors searched for the effect of IDE inhibitors on autoimmune diseases of the CNS, where immune activity takes place in excess, they found that these inhibitors are effective in the treatment and arrest of such diseases and suggest that they may be used in general for the treatment of diseases of the CNS.

As is shown in the Examples section which follows, the present inventors discovered that IDE−/− mice have a significant reduction in pro-inflammatory cytokines such as IL-17 and IFN-γ following spinal cord and myelin oligodendrocyte glycoprotein (MOG) 35-55 peptide immunization (see FIGS. 1A-F). Furthermore, IDE inhibitor reduced APC activation, as is shown by reduced secretion of IL-1β (FIG. 4B), and pro-inflammatory CD4+ T-cell activation, as is shown by reduced secretion of, IFN-γ (FIGS. 3A and 4A), IL-2 (FIG. 3B) and IL-6 (FIG. 3C). The use of an IDE inhibitor for therapeutic application in multiple sclerosis (MS) was studied. A nasal IDE inhibitor treatment, namely ADT-21 (SEQ ID NO: 6), initiated after disease onset reduced the clinical progression of chronic experimental autoimmune encephalomyelitis (EAE) in NOD mice immunized with myelin-oligodendrocyte glycoprotein (MOG, see FIG. 7). It is suggested that reducing IDE activity by specific inhibitors can be used as a novel therapeutic approach in EAE towards future intervention in MS.

While further reducing the present invention to practice, the present inventors have uncovered that nasal administering of an IDE inhibitor, ADT-21 (SEQ ID NO: 6), surprisingly improved the cognitive behavior of Alzheimer's animal model (see FIG. 8), reduced plaque load (see FIGS. 10A-C) and accelerated insulin levels in this mouse model (see FIG. 9). Thus, it is suggested that IDE inhibitors can be used as effective to drugs for the treatment of neurodegenerative diseases in general and Alzheimer's in particular.

Thus, according to one aspect of the present invention there is provided a method of treating a disease selected from the group consisting of an autoimmune disease of the central nervous system and a neurodegenerative disease, the method comprising administering to a subject in need thereof a therapeutically effective amount of an insulin degrading enzyme (IDE) inhibitor, thereby treating the disease.

According to another aspect, there is provided an insulin degrading enzyme (IDE) inhibitor for use in the treatment of a disease selected from the group consisting of an autoimmune disease of the central nervous system and a neurodegenerative disease.

The term "treating" refers to inhibiting or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

As used herein "an autoimmune disease of the central nervous system" refers to a disease where the body's immune system attacks its own nervous system (preferably CNS).

Examples of autoimmune diseases of the CNS include, but are not limited to, multiple sclerosis, Guillain-Barre syndrome, Lambert-Eaton myasthenic syndrome, Myasthenia gravis, transverse myelitis, progressive multifocal leukoencephalopathy, chronic headache, cerebral palsy, lupus, immune dysfunction muscular central nervous system breakdown, primary CNS vasculitis, autoimmune cerebellar degeneration, gait ataxia with late age onset polyneuropathy (GALOP), neuromyelitis optica, Stiff Person Syndrome and HTLV-1-associated myelopathy (HAM)/tropical spastic paraparesis (TSP).

According to a specific embodiment, the autoimmune disease of the central nervous system comprises multiple sclerosis (MS).

As used herein "a neurodegenerative disease" refers to a disorder, disease or condition of the nervous system (preferably CNS) which is characterized by gradual and progressive loss of neural tissue, neurotransmitter, or neural functions.

Examples of neurodegenerative disorder include, but are not limited to, amyotrophic lateral sclerosis (ALS or Lou Gehrig's Disease), autoimmune encephalomyelitis, degenerative nerve diseases, encephalitis (e.g. Rasmussen's encephalitis), Alzheimer's disease, epilepsy, genetic brain disorders, stroke, Parkinson's disease and Huntington's disease.

According to a specific embodiment, the neurodegenerative disease comprises an Alzheimer's disease.

As used herein "an insulin degrading enzyme (IDE) inhibitor" refers to a molecule that reduces the activity or expression of IDE (i.e. comprises an IDE inhibitory activity).

As used herein "an insulin degrading enzyme (IDE)" refers to the insulysin or insulin protease, a large zinc-binding protease of the M16A metalloprotease subfamily which is involved in the cellular processing of multiple short polypeptides including amyloid β-protein (Aβ), insulin, glucagon, amylin, atrial natriuretic factor and calcitonin (e.g., as set forth in GenBank Accession Nos. NM_004969 and NP_004960). An exemplary IDE of the present invention is set forth in EC 3.4.24.56.

The IDE inhibitor of the present teachings specifically down-regulates the enzymatic activity of IDE. For instance, the IC50 of IDE is in the range of 10-200 nM as assayed for ADT-21. According to exemplary embodiments, the IDE inhibitor of the present invention is capable of down-regulating by at least 5%, at least 10%, at least 15%, at least 20%, at least 30%, at least 40%, at least 50%, at least 60%, at least 70%, at least 80%, at least 90% or at least 100% the enzymatic activity of IDE.

It will be appreciated that IDE is a cellular enzyme which comprises an extracellular domain for substrate binding. Furthermore, IDE may also be secreted from the cells and thus, may bind its substrates extracellularly [Li et al. (2006) Cell 127:305-316; Shen et al. (2006) Nature 443:870-874]. Thus, it is envisioned by the present inventors that IDE will be inhibited by contacting on the cell surface or extracellularly.

It will be appreciated that the IDE inhibitor of the present invention is capable of reducing secretion of pro-inflammatory cytokines, such as IFN-γ and IL-17, from T lymphocytes (as depicted in Example 1 hereinbelow).

As used herein, the term "pro-inflammatory cytokines" refers to cytokines which promote systemic inflammation. Exemplary pro-inflammatory cytokines include, but are not limited to, IFN-γ, IL-17, INF-γ, IL-17, TNFα, IL-6, IL-2 and IL-1γ.

Methods of measuring levels of pro-inflammatory cytokines are well known in the art and include ELISA kit assays available e.g. from R&D Systems.

Furthermore, IDE inhibitory activity of the peptide of the present invention results in delayed progression of multiples sclerosis (as depicted in Example 1 hereinbelow), in elevated insulin levels (as depicted in Example 2 hereinbelow) and in improved cognitive behavior of Alzheimer's disease (as depicted in Example 2 hereinbelow).

Any method known in the art for measuring IDE activity may be used to assess down-regulation in IDE. For example, one method which may be used comprises the use of an Insulysin/IDE Immunocapture Activity Assay Kit (available e.g. from InnoZyme™, Calbiochem). Using this kit ELISA plates are first coated with the target enzyme (i.e. IDE) and then the plates are incubated with a substrate (e.g. insulin). The enzymatic activity is measured in comparison to wells without the substrate using for example a FRET substrate, Mca-GGFLRKHGQ-EDDnp (SEQ ID NO: 79). Cleavage of the scissile amide bond between R and K releases the fluorophore from the quenching molecule, Dnp, resulting in an increase in fluorescence. The increase in fluorescence is measured using an excitation wavelength of 320 nm and an emission wavelength of 405 nm.

Down-regulating IDE can be effected on the protein level using e.g., peptide inhibitors, small molecule inhibitors or antibodies, or on the genomic and/or the transcript level using a variety of molecules which interfere with transcription and/or translation (e.g., RNA silencing agents, Ribozyme, DNAzyme and antisense).

Thus, according to one embodiment of the present invention, the IDE inhibitor comprises a peptide inhibitor.

The term "peptide" as used herein encompasses native isolated peptides (either degradation products, synthetically synthesized peptides or recombinant peptides) and peptidomimetics (typically, synthetically synthesized peptides), as well as peptoids and semipeptoids which are peptide analogs, which may have, for example, at least one modification (e.g., synthetic i.e., non-naturally occurring) rendering the peptides more stable while in a body or more capable of penetrating into cells. Such modifications are further described hereinbelow. The peptide is at least a di-peptide as described below.

According to an embodiment of the present invention, the peptide is no more than 2 amino acids in length, no more than 4 amino acids in length, no more than 6 amino acids in length, no more than 8 amino acids in length, no more than 10 amino acids in length, no more than 15 amino acids in length, no more than 20 amino acids in length or no more than 25 amino acids in length.

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |

TABLE 1-continued

| Amino Acid | Three-Letter Abbreviation | One-letter Symbol |
|---|---|---|
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methyl-butyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | αethyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)-glycine | Ngln |
| D-α-methylornithine | Dmorn | N-(carbamylmethyl)-glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |

TABLE 2-continued

| Non-conventional amino acid | Code | Non-conventional amino acid | Code |
|---|---|---|---|
| D-α-methylcysteine | Dnmcys | N-(3,3-diphenylpropyl)glycine | Nbhe |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methyl-cyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α thylglutamine | Mgln | L-α-methylglutamate | Mglu |
| L-α-methylhistidine | Mhis | L-α-methyl-homo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methyl-cyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α ethylhistidine | Mhis | L-α-methylhomophenylalanine | Mhphe |
| L-α thylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α ethylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino) cyclopropane | Nmbc | | |

The peptides of the present invention may comprise modifications. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Conservative substitutions may be employed (e.g., as mentioned for the aspartate or homologs thereof, above). Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

According to one embodiment, the peptides of the present invention comprise at least one aspartate or a homolog thereof.

As used herein, the term "aspartate or homolog thereof" refers to the amino acid aspartic acid or to an amino acid with a structural homology thereto. According to an exemplary embodiment, the structural homolog is asparagine. According to other exemplary embodiments the homolog is a negatively charged amino acid such as, but not limited to, glutamic acid.

According to an exemplary embodiment of the invention, the peptide may comprise one, two or more aspartates or homologues thereof. According to an exemplary embodiment, the peptide comprises two asparates or homologues thereof.

According to one embodiment of this aspect of the present invention, the aspartates or homologous thereof are positioned consecutively in the peptide. An exemplary peptide of the present invention is as set forth in SEQ ID NO: 11.

It will be appreciated, that the aspartate or homolog thereof may be positioned to anywhere within the peptide, such as within the N-terminus of the peptide, the C-terminus of the peptide or within the IDE catalytic cleft binding site of the peptide as to enable specific binding and inhibition of IDE by the peptide of the present invention. Thus, an exemplary amino acid sequence of the peptide of the present invention is as set forth in SEQ ID NOs: 1-5 and SEQ ID NOs: 12-16.

According to an embodiment of the present invention, the peptide may comprise an at least one IDE binding sequence (e.g., 1, 2, 3 or more) as for example set forth in SEQ ID NOs: 72-76. This sequence may be positioned anywhere in the peptide such as at the N-terminus of the peptide or C-terminus of the peptide.

It will be appreciated that the peptide of the present invention may further comprise a moiety which adds flexibility. Such a moiety may add flexibility to the peptide and allow conformational flexibility for increased binding and inhibition of IDE. A moiety which adds flexibility of the present teachings may include a peptide moiety or a chemical moiety, such as an organic polymer. It will be appreciated that the moiety which adds flexibility may comprise a covalent bond (e.g. a peptide bond) or a non-covalent bond.

Exemplary chemical crosslinking methods for moieties which add flexibility of the present invention are described herein below:

Thiol-Amine Crosslinking:

In this scheme, an amine group of the peptide is indirectly conjugated to a thiol group, usually by a two- or three-step reaction sequence. The high reactivity of thiols and their relative rarity in most peptides make thiol groups ideal targets for controlled chemical crosslinking. Thiol groups may be introduced into the peptide using one of several thiolation methods including SPDP. The thiol-containing biomolecule is then reacted with an amine-containing biomolecule using a heterobifunctional crosslinking reagent.

Amine-Amine Crosslinking:

Conjugation of the moiety element can be accomplished by methods known to those skilled in the art using amine-amine crosslinkers including, but not limited to glutaraldehyde, bis (imido esters), bis(succinimidyl esters), diisocyanates and diacid chlorides.

Carbodiimide Conjugation:

Conjugation of the moiety element can be accomplished by methods known to those skilled in the art using a dehydrating agent such as a carbodiimide. Most preferably the carbodiimide is used in the presence of 4-dimethyl aminopyridine. As is well known to those skilled in the art, carbodiimide conjugation can be used to form a covalent bond between a carboxyl group of one peptide and an hydroxyl group of a second peptide (resulting in the formation of an ester bond), or an amino group of a second peptide (resulting in the formation of an amide bond) or a sulfhydryl group of a second peptide (resulting in the formation of a thioester bond).

Likewise, carbodiimide coupling can be used to form analogous covalent bonds between a carbon group of a first peptide and an hydroxyl, amino or sulfhydryl group of a second peptide. See, generally, J. March, Advanced Organic Chemistry: Reaction's, Mechanism, and Structure, pp. 349-50 & 372-74 (3d ed.), 1985.

An exemplary moiety which adds flexibility of the present invention comprises an amino acid sequence, such as set forth in SEQ ID NO: 77.

It will be appreciated that the amino acid sequence of the moiety which adds flexibility may be positioned at any position within the peptide as to allow conformational flexibility, as for example, between the aspartate or homolog thereof and the N-terminus sequence of the present invention.

Thus, according to another embodiment, the amino acid sequence of the peptide of the present invention is as set forth in SEQ ID NOs: 6-10 and SEQ ID NOs: 17-36. According to an exemplary embodiment, the amino acid sequence is as set forth in SEQ ID NO: 6.

According to one embodiment, the peptide inhibitor is a peptide which includes an amino acid sequence being no more than 25 amino acids in length, the amino acid sequence comprising at least one aspartate or a homolog thereof, the peptide having an IDE inhibitory activity.

Exemplary peptide inhibitors of the present invention are listed in the Table 3, below.

TABLE 3

IDE inhibitory peptides

| No. | Peptide | Amino acid sequence |
|---|---|---|
| 1 | ADT-1 | VLRYDDFHTD (SEQ ID NO: 1) |
| 2 | ADT-2 | EALYDDLVCG (SEQ ID NO: 2) |
| 3 | ADT-3 | LANFDDLVHSSNN (SEQ ID NO: 3) |
| 4 | ADT-4 | FVQWDDLMN (SEQ ID NO: 4) |
| 5 | ADT-5 | KLVFDDFAED (SEQ ID NO: 5) |
| 6 | ADT-21 | ITNPGSGGSSVLRYDDFHTD (SEQ ID NO: 6) |
| 7 | ADT-22 | FVNQGSGGSSEALYDDLVCG (SEQ ID NO: 7) |
| 8 | ADT-23 | KCNTGSGGSSLANFDDLVHSSNN (SEQ ID NO: 8) |
| 9 | ADT-24 | HSQGGSGGSSFVQWDDLMN (SEQ ID NO: 9) |
| 10 | ADT-25 | DAEFGSGGSSKLVFDDFAED (SEQ ID NO: 10) |
| 11 | ADT-31 | DD (SEQ ID NO: 11) |
| 12 | ADT-32 | DDEALYLVCG (SEQ ID NO: 12) |
| 13 | ADT-33 | EALYNNLVCG (SEQ ID NO: 13) |
| 14 | ADT-34 | EALYAALVCG (SEQ ID NO: 14) |
| 15 | ADT-35 | EALYFFLVCG (SEQ ID NO: 15) |

TABLE 3-continued

IDE inhibitory peptides

| No. | Peptide | Amino acid sequence |
|---|---|---|
| 16 | ADT-36 | EALYEELVCG (SEQ ID NO: 16) |
| 17 | ADT-41 | ITNPGSGGSSEALYDDLVCG (SEQ ID NO: 17) |
| 18 | ADT-42 | ITNPGSGGSSLANFDDLVHSSNN (SEQ ID NO: 18) |
| 19 | ADT-43 | ITNPGSGGSSFVQWDDLMN (SEQ ID NO: 19) |
| 20 | ADT-44 | ITNPGSGGSSKLVFDDFAED (SEQ ID NO: 20) |
| 21 | ADT-51 | FVNQGSGGSSVLRYDDFHTD (SEQ ID NO: 21) |
| 22 | ADT-52 | FVNQGSGGSSLANFDDLVHSSNN (SEQ ID NO: 22) |
| 23 | ADT-53 | FVNQGSGGSSFVQWDDLMN (SEQ ID NO: 23) |
| 24 | ADT-54 | FVNQGSGGSSKLVFDDFAED (SEQ ID NO: 24) |
| 25 | ADT-61 | KCNTGSGGSSVLRYDDFHTD (SEQ ID NO: 25) |
| 26 | ADT-62 | KCNTGSGGSSEALYDDLVCG (SEQ ID NO: 26) |
| 27 | ADT-63 | KCNTGSGGSSFVQWDDLMN (SEQ ID NO: 27) |
| 28 | ADT-64 | KCNTGSGGSSKLVFDDFAED (SEQ ID NO: 28) |
| 29 | ADT-71 | HSQGSGGSSVLRYDDFHTD (SEQ ID NO: 29) |
| 30 | ADT-72 | HSQGSGGSSEALYDDLVCG (SEQ ID NO: 30) |
| 31 | ADT-73 | HSQGSGGSSLANFDDLVHSSNN (SEQ ID NO: 31) |
| 32 | ADT-74 | HSQGSGGSSKLVFDDFAED (SEQ ID NO: 32) |
| 33 | ADT-81 | DAEFGSGGSSVLRYDDFHTD (SEQ ID NO: 33) |
| 34 | ADT-82 | DAEFGSGGSSEALYDDLVCG (SEQ ID NO: 34) |
| 35 | ADT-83 | DAEFGSGGSSLANFDDLVHSSNN (SEQ ID NO: 35) |
| 36 | ADT-84 | DAEFGSGGSSFVQWDDLMN (SEQ ID NO: 36) |

The peptides of the present invention are preferably utilized in a linear form, although it will be appreciated that in cases where cyclization does not severely interfere with peptide characteristics, cyclic forms of the peptide can also be utilized.

It will be appreciated that since one of the main obstacles in using short peptide fragments in therapy is their proteolytic degradation by stereospecific cellular proteases, the peptides of the present invention preferably comprise at least one D-isomer of natural amino acids [i.e., inverso peptide analogues, Tjernberg (1997) J. Biol. Chem. 272:12601-5].

The peptides of the present invention may be synthesized by any techniques that to are known to those skilled in the art of peptide synthesis, such as by using standard solid phase techniques. These methods include exclusive solid phase synthesis, partial solid phase synthesis methods, fragment condensation, classical solution synthesis. Solid phase peptide synthesis procedures are well known in the art and further described by John Morrow Stewart and Janis Dillaha Young, Solid Phase Polypeptide Syntheses (2nd Ed., Pierce Chemical Company, 1984).

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the peptide compounds of the present invention involves solid phase peptide synthesis.

Large scale peptide synthesis is described by Andersson Biopolymers 2000; 55(3):227-50.

Recombinant techniques may also be used to generate the peptides of the present invention. To produce a peptide of the present invention using recombinant technology, a nucleotide sequence (such as listed in Table 4 below) encoding a peptide of the present invention is ligated into a nucleic acid expression vector, which comprises the nucleotide sequence under the transcriptional control of a cis-regulatory sequence (e.g., to promoter sequence) suitable for directing constitutive, tissue specific or inducible transcription of the peptides of the present invention in the host cells.

TABLE 4

Exemplary nucleotide sequences of peptides of some embodiments of the present invention

| No. | Peptide | Sequence 5'-3' |
|---|---|---|
| 1 | ADT-1 | Gtgctgcgctatgatgattttcataccgat (SEQ ID NO: 37) |

TABLE 4-continued

Exemplary nucleotide sequences of peptides of some embodiments of the present invention

| No. | Peptide | Sequence 5'-3' |
|---|---|---|
| 2 | ADT-2 | Gaagcgctgtatgatgatctggtgtgcggc (SEQ ID NO: 38) |
| 3 | ADT-3 | Ctggcgaactttgatgatctggtgcatagcagcaacaac (SEQ ID NO: 39) |
| 4 | ADT-4 | Tttgtgcagtgggatgatctgatgaac (SEQ ID NO: 40) |
| 5 | ADT-5 | Aaactggtgtttgatgattttgcggaagat (SEQ ID NO: 41) |
| 6 | ADT-21 | Attaccaacccgggcagcggcggcagcagcgtgctgcgctatgatgattttcataccgat (SEQ ID NO: 42) |
| 7 | ADT-22 | Tttgtgaaccagggcagcggcggcagcagcgaagcgctgtatgatgatctggtgtgcggc (SEQ ID NO: 43) |
| 8 | ADT-23 | Aaatgcaacaccggcagcggcggcagcagcctggcgaactttgatgatctggtgcatagcagcaacaac (SEQ ID NO: 44) |
| 9 | ADT-24 | Catagccagggcggcagcggcggcagcagctttgtgcagtgggatgatctgatgaac (SEQ ID NO: 45) |
| 10 | ADT-25 | Gatgcggaatttggcagcggcggcagcagcaaactggtgtttgatgattttgcggaagat (SEQ ID NO: 46) |
| 11 | ADT-31 | Gatgat (SEQ ID NO: 47) |
| 12 | ADT-32 | Gatgatgaagcgctgtatctggtgtgcggc (SEQ ID NO: 48) |
| 13 | ADT-33 | Gaagcgctgtataacaacctggtgtgcggc (SEQ ID NO: 49) |
| 14 | ADT-34 | Gaagcgctgtatgcggcgctggtgtgcggc (SEQ ID NO: 50) |
| 15 | ADT-35 | Gaagcgctgtattttttttctggtgtgcggc (SEQ ID NO: 51) |
| 16 | ADT-41 | Attaccaacccgggcagcggcggcagcagcgaagcgctgtatgatgatctggtgtgcggc (SEQ ID NO: 52) |
| 17 | ADT-42 | Attaccaacccgggcagcggcggcagcagcctggcgaactttgatgatctggtgcatagcagcaacaac (SEQ ID NO: 53) |
| 18 | ADT-43 | attaccaacccgggcagcggcggcagcagctttgtgcagtgggatgatctgatgaac (SEQ ID NO: 54) |
| 19 | ADT-44 | attaccaacccgggcagcggcggcagcagcaaactggtgtttgatgattttgcggaagat (SEQ ID NO: 55) |
| 20 | ADT-51 | tttgtgaaccagggcagcggcggcagcagcgtgctgcgctatgatgattttcataccgat (SEQ ID NO: 56) |
| 21 | ADT-52 | tttgtgaaccagggcagcggcggcagcagcctggcgaactttgatgatctggtgcatagcagcaacaac (SEQ ID NO: 57) |
| 22 | ADT-53 | tttgtgaaccagggcagcggcggcagcagctttgtgcagtgggatgatctgatgaac (SEQ ID NO: 58) |
| 23 | ADT-54 | tttgtgaaccagggcagcggcggcagcagcaaactggtgtttgatgattttgcggaagat (SEQ ID NO: 59) |
| 24 | ADT-61 | aaatgcaacaccggcagcggcggcagcagcgtgctgcgctatgatgattttcataccgat (SEQ ID NO: 60) |
| 25 | ADT-62 | aaatgcaacaccggcagcggcggcagcagcgaagcgctgtatgatgatctggtgtgcggc (SEQ ID NO: 61) |
| 26 | ADT-63 | aaatgcaacaccggcagcggcggcagcagctttgtgcagtgggatgatctgatgaac (SEQ ID NO: 62) |

TABLE 4-continued

Exemplary nucleotide sequences of peptides of some embodiments of the present invention

| No. | Peptide | Sequence 5'-3' |
|---|---|---|
| 27 | ADT-64 | aaatgcaacaccggcagcggcggcagcagcaaactggtgtttgatgattttgcggaagat (SEQ ID NO: 63) |
| 28 | ADT-71 | catagccagggcggcagcggcggcagcagcgtgctgcgctatgatgattttcataccgat (SEQ ID NO: 64) |
| 29 | ADT-72 | catagccagggcggcagcggcggcagcagcgaagcgctgtatgatgatctggtgtgcggc (SEQ ID NO: 65) |
| 30 | ADT-73 | catagccagggcggcagcggcggcagcagcctggcgaactttgatgatctggtgcatagcagcaacaac (SEQ ID NO: 66) |
| 31 | ADT-74 | catagccagggcggcagcggcggcagcagcaaactggtgtttgatgattttgcggaagat (SEQ ID NO: 67) |
| 32 | AM-81 | gatgcggaatttggcagcggcggcagcagcgtgctgcgctatgatgattttcataccgat (SEQ ID NO: 68) |
| 33 | ADT-82 | gatgcggaatttggcagcggcggcagcagcgaagcgctgtatgatgatctggtgtgcggc (SEQ ID NO: 69) |
| 34 | ADT-83 | gatgcggaatttggcagcggcggcagcagcctggcgaactttgatgatctggtgcatagcagcaacaac (SEQ ID NO: 70) |
| 35 | ADT-84 | Gatgcggaatttggcagcggcggcagcagctttgtgcagtgggatgatctgatgaac (SEQ ID NO: 71) |

Constitutive promoters suitable for use with the present invention are promoter sequences which are active under most environmental conditions and most types of cells such as the cytomegalovirus (CMV) and Rous sarcoma virus (RSV). Inducible promoters suitable for use with the present invention include for example the tetracycline-inducible promoter (Zabala M, et al., Cancer Res. 2004, 64(8): 2799-804).

Other than containing the necessary elements for the transcription of the inserted coding sequence, the expression construct of the present invention can also include sequences engineered to enhance stability, production, purification, yield or toxicity of the expressed RNA. Recombinant synthesis is well known in the art and can also be used to synthesize the peptide in vivo using the appropriate transcription and translation elements.

In addition to being synthesizable in host cells, the peptide of the present invention can also be synthesized using in vitro expression systems. These methods are well known in the art and the components of the system are commercially available.

According to another embodiment of the present invention, the IDE inhibitor is a small molecule inhibitor.

Examples of small molecule inhibitors of the present invention include, but are not limited to, N-Ethylmaleimide, p-chloromercuribenzoic acid, 1,10-phenanthroline, bacitracin or hydroxamate inhibitor.

Thus, for example, the hydroxamate inhibitor may comprise the formula:

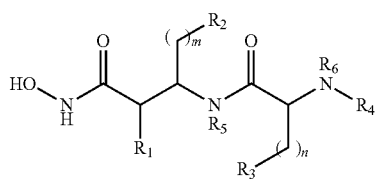

wherein $R_1$, $R_2$, $R_3$, $R_4$, $R_5$ and $R_6$ are independently selected and wherein $R_1$ is H, OH, O-alkyl or alkyl, $R_2$ is aryl, heteroaryl, Ph, 1-naphthyl, 2-naphthyl, substituted Ph, substituted 1-naphthyl, or substituted 2-naphthyl, $R_3$ is NHC($=$NH)NH$_2$, NH$_2$, NHC(O)alkyl, or NHC(O)aryl, $R_4$ is [C($=$O)CH(CH$_2$)$_o$R$_7$NH]$_p$H or [C($=$O)CH(CH$_2$)$_o$R$_7$NH]$_p$C($=$O)Me, $R_5$ is H or Me, $R_6$ is H or Me, $R_7$ is 4-hydroxyphenyl, CO$_2$H, indol-3-yl, or phenyl, m is 0-3, n is 0-3, o is 0-3 and p is 0-2. Furthermore, according to a specific embodiment, $R_2$ is 2-naphthyl, and $R_3$ is NHC($=$NH)NH$_2$.

Any methods known in the art for synthesizing small molecules may be used in accordance with the present teachings.

Methods of synthesizing and utilizing hydroxamate inhibitors are described in length in WO2008156701A2: "hydroxamate inhibitors of insulin-degrading enzyme and uses thereof", which is hereby incorporated by reference in its entirety.

Methods of synthesizing phenanthroline are described e.g. in Halcrow and Kermack (1946) 43. Attempts to find new antimalarials. Part XXIV. Derivatives of o-phenanthroline (7:8:3': 2'-pyridoquinoline). J. Chem. Soc.: 155-157. In short, phenanthroline molecules may be prepared by two successive Skraup reactions of to glycerol with o-phenylenediamine, catalyzed by sulfuric acid, and an oxidizing agent, traditionally aqueous arsenic acid or nitrobenzene. Dehydration of glycerol gives acrolein which condenses with the amine followed by a cyclization.

Bacitracin may be synthesized via non-ribosomal peptide synthetases (NRPSs) or by solid-phase total synthesis [see e.g. Lee and Griffin (1996) J. Org. Chem., 61 (12), pp 3983-3986].

Alternatively, the small molecules of the present invention may be purchased from any manufacturer, e.g. Bacitracin may be bought from e.g. Sigma-Aldrich.

Another example, of an agent capable of down-regulating an IDE is an antibody or antibody fragment capable of specifically binding IDE. Preferably, the antibody specifically binds at least one epitope of an IDE. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')$_2$, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single to polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab') .sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it to from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Exemplary antibodies which may be used according to the present teachings include monoclonal anti-IDE antibodies (e.g. anti-IDE 9B12) available e.g. from Covance, Abcam, Abbiotec, Abnova Corporation and ABR.

According to another embodiment, the IDE inhibitor may comprise a nucleic acid agent for silencing IDE expression.

Downregulation of IDE can be achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of inhibiting or "silencing" the expression of a target gene. In certain embodiments, the RNA silencing agent is capable of preventing complete processing (e.g., the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into to short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, the present invention contemplates use of dsRNA to down-regulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl. Acad. Sci. USA. 2002; 99:1443-1448; Tran N., et al., FEBS Lett. 2004; 573: 127-134].

In particular, the present invention also contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The present invention also contemplates introduction of long dsRNA specifically designed not to induce the interferon and PKR pathways for down-regulating gene expression. For example, Shinagwa and Ishii [Genes & Dev. 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21 mers with a central 19 bp duplex region and symmetric 2-base 3'-overhangs on the termini, although it has been recently described that chemically synthesized RNA duplexes of 25-30 base length can have as much as a 100-fold increase in potency compared with 21 mers at the same location. The observed increased potency obtained using longer RNAs in triggering RNAi is theorized to result from providing Dicer with a substrate (27 mer) instead of a product (21 mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of the present invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

Exemplary siRNAs which may be used according to the present teachings include, for example, those available from Dharmacon—IDE-specific siRNA SmartPools (siRNA-IDE1 and siRNA-IDE2), or human IDE siRNA (sc-106817) available from Santa Cruz Biotechnology, Inc.

Exemplary shRNAs which may be used according to the present teachings include, for example, human IDE shRNA plasmid (sc-106817-SH) and human IDE shRNA lentiviral particles (sc-106817-V) both available from Santa Cruz Biotechnology, Inc.

According to another embodiment the RNA silencing agent may be a miRNA. miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target) The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A recent report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

Synthesis of RNA silencing agents suitable for use with the present invention can be effected as follows. First, the IDE mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tusch1 ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (wwwdotambiondotcom/techlib/tn/91/912dothtml).

Second, potential target sites are compared to an appropriate genomic database (e.g., human, mouse, rat etc.) using any sequence alignment software, such as the BLAST software available from the NCBI server (wwwdotncbidotnlmdotnih-dotgov/BLAST/). Putative target sites which exhibit significant homology to other coding sequences are filtered out.

Qualifying target sequences are selected as template for siRNA synthesis. Preferred sequences are those including low G/C content as these have proven to be to more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

For example, a suitable IDE siRNA can be the siRNA ID IDE (Ambion Inc., Austin, Tex.)

It will be appreciated that the RNA silencing agent of the present invention need not be limited to those molecules containing only RNA, but further encompasses chemically-modified nucleotides and non-nucleotides.

In some embodiments, the RNA silencing agent provided herein can be functionally associated with a cell-penetrating peptide. As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of the present invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of the present invention preferably include, but are not limited to, penetratin, transportan, pIs1, TAT(48-60), pVEC, MTS, and MAP.

mRNAs to be targeted using RNA silencing agents include, but are not limited to, those whose expression is correlated with an undesired phenotypic trait. Exemplary mRNAs that may be targeted are those that encode truncated proteins i.e. comprise deletions. Accordingly the RNA silencing agent of the present invention may be targeted to a bridging region on either side of the deletion. Introduction of such RNA silencing agents into a cell would cause a down-regulation of the mutated protein while to leaving the non-mutated protein unaffected.

Downregulation of an IDE can also be effected by using an antisense polynucleotide capable of specifically hybridizing with an mRNA transcript encoding the IDE.

Design of antisense molecules which can be used to efficiently downregulate an IDE must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., to Nature Biotechnology 16: 1374-1375 (1998)].

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)].

More recently, antisense-mediated suppression of human heparanase gene expression has been reported to inhibit pleural dissemination of human cancer cells in a mouse model [Uno et al., Cancer Res 61:7855-60 (2001)].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another agent capable of downregulating an IDE is a ribozyme molecule capable of specifically cleaving an mRNA transcript encoding an IDE. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have to demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Following synthesis, any of the above-mentioned inhibitors of the present invention may optionally be tested for their IDE inhibitory activity.

For IDE inhibition intracellularly, any of the above inhibitors can be attached to cell penetrating moieties.

Thus, the IDE peptide inhibitor of the present invention may be attached (either covalently or non-covalently) to a penetrating agent.

As used herein the phrase "penetrating agent" refers to an agent which enhances translocation of any of the attached peptides across a cell membrane.

According to one embodiment, the penetrating agent is a peptide and is attached to the IDE peptide inhibitor (either directly or non-directly) via a peptide bond.

Typically, peptide penetrating agents have an amino acid composition containing either a high relative abundance of positively charged amino acids such as lysine or arginine, or have sequences that contain an alternating pattern of polar/charged amino acids and non-polar, hydrophobic amino acids.

Examples of peptide penetrating agents include those set forth in SEQ ID NOs: 80-82. By way of non-limiting example, cell penetrating peptide (CPP) sequences may be used in order to enhance intracellular penetration. CPPs may included short and long versions of TAT (YGRKKRR—SEQ ID NO: 80 and YGRKKRRQRRR—SEQ ID NO: 81) and PTD (RRQRR—SEQ ID NO: 82). However, the disclosure is not so limited, and any suitable penetrating agent may be used, as known by those of skill in the art.

Various methods, widely practiced in the art, may be employed to attach or conjugate the cell penetrating moieties to the IDE peptide inhibitors of the present invention, depending on the context, application and purpose.

When the cell penetrating moiety is a polypeptide, the immunoconjugate may be produced by recombinant means. For example, the nucleic acid sequence encoding the penetrating agent (e.g. SEQ ID NOs: 80-82) may be ligated in-frame with the nucleic acid sequence encoding the peptide inhibitors (e.g., SEQ ID NOs: 37-71) and be to expressed in a host cell to produce a recombinant conjugated polypeptide. Alternatively, the cell penetrating moiety may be chemically synthesized by, for example, the stepwise addition of one or more amino acid residues in defined order such as solid phase peptide synthetic techniques.

A cell penetrating moiety may also be attached to the IDE peptide inhibitor of the invention using standard chemical synthesis techniques widely practiced in the art [see e.g., hypertexttransferprotocol://worldwideweb (dot) chemistry (dot) org/portal/Chemistry)], such as using any suitable chemical linkage, direct or indirect, as via a peptide bond (when the cell penetrating moiety is a polypeptide), or via covalent bonding to an intervening linker element, such as a linker peptide or other chemical moiety, such as an organic polymer. Chimeric peptides may be linked via bonding at the carboxy (C) or amino (N) termini of the peptides, or via bonding to internal chemical groups such as straight, branched or cyclic side chains, internal carbon or nitrogen atoms, and the like.

Exemplary methods for conjugating peptide moieties to the IDE peptide inhibitors of the invention include, but are not limited to, SPDP conjugation as described in Cumber et al. (1985, Methods of Enzymology 112: 207-224), glutaraldehyde conjugation as described in G. T. Hermanson (1996, "Antibody Modification and Conjugation, in Bioconjugate Techniques, Academic Press, San Diego), carbodiimide conjugation [see, J. March, Advanced Organic Chemistry: Reaction's, Mechanism, and Structure, pp. 349-50 & 372-74 (3d ed.), 1985].

It will be appreciated that other cell penetrating agents may be used for delivery of the non-peptide IDE inhibitors of the present invention (e.g. small molecules or nucleic acid agent) into a cell.

According to an embodiment, lipid particles such as liposomes are used as cell penetrating agents.

Liposomes include any synthetic (i.e., not naturally occurring) structure composed of lipid bilayers, which enclose a volume. Liposomes include emulsions, foams, micelles, insoluble monolayers, liquid crystals, phospholipid dispersions, lamellar layers and the like. The liposomes may be prepared by any of the known to methods in the art [Monkkonen, J. et al., 1994, J. Drug Target, 2:299-308; Monkkonen, J. et al., 1993, Calcif. Tissue Int., 53:139-145; Lasic D D., Liposomes Technology Inc., Elsevier, 1993, 63-105. (chapter 3); Winterhalter M, Lasic D D, Chem Phys Lipids, 1993 September; 64(1-3):35-43]. The liposomes may be positively charged, neutral or negatively charged. For Mononuclear Phagocyte System (MPS) uptake, the liposomes can be hydrophobic since hydrophilic masking of the liposome membrane (e.g., by use of polytheleneglycol-linked lipids and hydrophilic particles) may be less prone to MPS uptake. It is also preferable that the liposomes do not comprise sterically shielded lipids such as ganglioside-$GM_1$ and phosphatidylinositol since these lipids prevent MPS uptake.

The liposomes may be a single lipid layer or may be multilamellar. If the therapeutic agent is hydrophilic, its delivery may be further improved using large unilamellar vesicles because of their greater internal volume. Conversely, if the therapeutic agent is hydrophobic, its delivery may be further improved using multilamellar vesicles. Alternatively, the therapeutic agent (e.g. oligonucleotide) may not be able to penetrate the lipid bilayer and consequently would remain adsorbed to the liposome surface. In this case, increasing the surface area of the liposome may further improve delivery of the therapeutic agent. Suitable liposomes in accordance with the invention are non-toxic liposomes such as, for example, those prepared from phosphatidyl-choline phosphoglycerol, and cholesterol. The diameter of the liposomes used can range from 0.1-1.0 microns. However, other size ranges suitable for phagocytosis by phagocytic cells may also be used. For sizing liposomes, homogenization may be used, which relies on shearing energy to fragment large liposomes into smaller ones. Homogenizers which may be conveniently used include microfluidizers produced by Microfluidics of Boston, Mass. In a typical homogenization procedure, liposomes are recirculated through a standard emulsion homogenizer until selected liposomes sizes are observed. The particle size distribution can be monitored by conventional laser beam particle size discrimination. Extrusion of liposomes through a small-pore polycarbonate membrane or an asymmetric ceramic membrane is an effective method for reducing liposome sizes to a relatively well defined size distribution. Typically, the suspension is cycled through the membrane one or more times until the desired liposome size distribution is achieved. The liposomes may be extruded through successively smaller pore membranes to achieve a gradual reduction in liposome size.

Any method known in the art can be used to incorporate an IDE inhibitor (e.g. small molecules or nucleic acid agent) into a liposome. For example, the IDE inhibitor may be encapsulated within the liposome. Alternatively, it may be adsorbed on the liposome's surface. Other methods that may be used to incorporate a pharmaceutical agent into a liposome of the present invention are those described by Alfonso et al., [The science and practice of pharmacy, Mack Publishing, Easton Pa. $19^{th}$ ed., (1995)] and those described by Kulkarni et al., [J. Microencapsul.1995, 12 (3) 229-46].

The liposomes used in the methods of the present invention preferably cross the blood barriers. Thus, the liposomes of the present invention preferably do not comprise a blood barrier targeting polysaccharide (e.g. mannose) in their membrane portion. Preferably, the liposomes of the present invention do not comprise peptides in their membrane portion that target the liposomes to a receptor on a blood bather. Examples of such peptides include but are not limited to transferrin, insulin, IGF-1, IGF-2 anti-transferrin receptor antibody, anti-insulin receptor antibody, anti-IGF-1 receptor antibody and anti-IGF-2 receptor antibody.

In order to determine liposomes that are especially suitable in accordance with the present invention a screening assay can be performed such as the assays described in U.S. Pat. Appl. No. 20040266734 and U.S. Pat. Appl. No. 20040266734; and in Danenberg et al., Journal of cardiovascular pharmacology 2003, 42:671-9; Circulation 2002, 106: 599-605; Circulation 2003, 108:2798-804.

Any of the above inhibitors can be administered to the subject per se or as part of a pharmaceutical composition. Preferably such compositions are formulated to allow passage through the blood brain bather (BBB).

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport to pathways of the BBB; pharmacological strategies designed to increase the lipid solubility of an agent (e.g., conjugation of water-soluble agents to lipid or cholesterol carriers, such as lipophilic tails, e.g. long chain alkyl, which enhance penetration or activity of the IDE inhibitors); and the transitory disruption of the integrity of the BBB by hyperosmotic disruption (resulting from the infusion of a mannitol solution into the carotid artery or the use of a biologically active agent such as an angiotensin peptide).

Methods for drug delivery behind the BBB include intracerebral implantation (such as with needles) and convection-enhanced distribution. Mannitol can be used in bypassing the BBB. Likewise, mucosal (e.g., nasal) administration can be used to bypass the BBB.

The peptides of the present invention can also be administered to an organism in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the peptide accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, to transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

According to a specific embodiment of the present invention, the polypeptide of the present invention is administered via nasal administration.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for to example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (peptide) effective to prevent, alleviate or ameliorate symptoms of a disorder (e.g., diabetes) or prolong the survival of the subject being treated.

According to an embodiment of the present invention, administration of the IDE inhibitor results in an increase in blood insulin levels of the subject.

According to yet another embodiment of the present invention, administration of the IDE inhibitor results in a reduction in secretion of pro-inflammatory cytokines (e.g. IFN-γ and/or IL-17) from T lymphocytes of the subject.

According to another embodiment of the present invention, administration of the peptide results in delayed progression or prevention of multiple sclerosis.

According to another embodiment of the present invention, administration of the peptide results in amelioration of symptoms and Aβ burden in Alzheimer's disease.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide sufficient plasma levels of the active ingredient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

For example, according to one embodiment, a peptide of the present invention (e.g. ADT21) may be administered at a dose between 0.1-10 µg per kg body weight.

It will be appreciated that animal models exist by which the peptides of the present invention may be tested prior to human treatment. For example, multiple sclerosis animal models include the murine EAE model (e.g. induction of disease in NOD mice by immunization with MOG35-55 in CFA, as described in detail in Example 1 below). Alzheimer's disease animal models include APP/PSI mice and Samaritan Alzheimer's Rat Model (available from Samaritan Pharmaceuticals).

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

It will be appreciated that the therapeutic compositions of the invention may comprise, in addition to the IDE inhibitors, other known medications for the treatment of autoimmune diseases or the CNS or neurodegenerative diseases such as, but not limited to, steroids, corticosteroids (e.g. prednisone), immunosuppressant drugs (e.g. cyclophosphamide, cyclosporine, azathioprine, tacrolimus), antihistamine drugs (e.g. dimebolin), insulin and insulin-like growth factor 1 (IGF1). These medications may be included in the article of manufacture in a single or in separate packagings.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination to in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example I

Effect of the Peptides of the Present Invention on Multiple Sclerosis

Materials and Experimental Procedures
Animals
8-10 week old NOD mice, C57BL/6 mice and IDE−/− mice were kept in a conventional pathogen-free facility at Tel-Aviv University, and all experiments were in accordance with Tel-Aviv University guidelines and approved by the Tel-Aviv University animal care committee of animal research.

In Vitro Culture of T Cells
10 weeks old C57BL/6 and in IDE−/− mice (n=3-4) were injected with 100 µg of homogenized mouse spinal cord as previously described [Aharoni et al., Eur. J. Immunol. (1993) 23: 17-25], the splenocytes were removed and cultured in the presence of 0.5 µg/ml anti-CD3 (R&D system).

Alternatively, splenocytes were removed and cultured in the presence of 100 µg/ml MOG35-55 (Novetide, Israel) and were plated in 96-well round-bottom plates in Dulbeco modified Eagle medium (supplemented with 10% FCS, 4 mM L-glutamine, 100 U/mL penicillin, 0.1 mg/mL streptomycin, and 1% sodium pyruvate and were to maintained at 37° C. in 5% CO2 and 95% relative humidity) at a concentration of $1 \times 10^6$ cells per well in the presence of 100 µg/ml $MOG_{35-55}$ for either 24 or 48 hrs, the medium was collected for cytokine measurements (as detailed below).

In Vitro Culture of T Cells with APCs

Splenocytes were isolated from mice 10 days after immunization with $MOG_{35-55}$ peptide and the CD4+ T cells were positively separated using magnetic beads according to the suggested protocol (BD-551539). Splenocyte antigen presenting cells (APCs) were isolated from non immunized WT mice or IDE−/− mice as described before (Ochi et al., Nature 2006). The isolated CD4+ T-cells were then co-cultured with APCs in the presence of 100 µg/ml MOG35-55 with or without an IDE inhibitor (ADT21-0.1 µM).

LPS Assay

Splenocytes from WT and IDE−/− mice were removed and cultured in the present of 0.1 ug/ml LPS (Sigma) for 24 h. Supernatant TNF-α and IL-6 cytokines where measured by ELISA (as detailed below).

Measurement of Pro-Inflammatory Cytokines

The levels of the secreted pro-inflammatory cytokines were measured by ELISA using commercially available kits: INF-γ (R&D Systems), IL-17 (R&D Systems), TNFα (R&D Systems), IL-6 (R&D Systems), IL-2 (R&D Systems) and IL-1γ (R&D Systems) as previously described (Weiss et al, BBI 2010).

Western-Blot Analysis

Cells of N9 microglia cell line were incubated with either 5 ng/ml or 10 ng/ml IFN-γ for 24 hours. IDE expression were measured using anti-IDE antibody (Abcam) as compared to GAPDH.

Measurement of Nitric Oxide

Nitrite levels (µM) were measured from cell culture supernatants (N9 microglia cell line cultures incubated with either 5 ng/ml or 10 ng/ml IFN-γ for 24 hours) using the Quantichrom Nitric Oxide assay kit (DINO-250).

Induction of Multiple Sclerosis (MS)

8-week-old C57BL/6 mice were immunized with MOG35-55 in CFA with 200 µl of an emulsion containing 250 µg of MOG35-55 peptide (MEVGWYRSPFSRVVH-LYRNGK, SEQ ID NO: 78) and 400 µg of *Mycobacterium tuberculosis* extract H37 Ra (Difco) in incomplete Freund's adjuvant oil. In addition, the animals received 250 ng of pertussis toxin (Biological Laboratories) i.p. on day 0 and day 2. Starting a day before the immunization and during the following 11 days, mice received nasal administrations of the IDE inhibitor, ADT21 (1.07 µg/mouse). PBS treated mice served as control.

Alternatively, EAE was induced in 10-week-old NOD mice by immunization with MOG35-55 in CFA with 200 µL of an emulsion containing 150 µg myelin oligodendrocyte glycoprotein (MOG) 35-55 peptide (as set forth in SEQ ID NO: 78) and 400 µg *Mycobacterium tuberculosis* extract H37 Ra (Difco) in incomplete Freund adjuvant oil. The animals also received 150 ng pertussis toxin (PT, Biological Laboratories) intraperitoneally (i.p.) on day 0 and day 2. 18 days after EAE induction, mice received every other day a nasal IDE inhibitor treatment (1.07 µg ADT21).

Clinical signs of EAE were assessed according to the following score: 0, no disease; 1, loss of tone in the tail; 2, hind limb weakness; 3, hind limb paralysis; 4, hind limb plus forelimb paralysis; 5, moribund state.

Results

Reduction of Pro-Inflammatory Cytokines Against Myelin Antigen in IDE−/− Mice

Recent research has suggested that Th17 and Th1 cells are involved in the pathogenesis of autoimmune diabetes [Honkanen et al. J Immunol (2010) 185:3:1959-67; Hrubec et al., Anat Rec (Hoboken) (2009) 292:2:271-6]. In order to investigate the effect of the IDE inhibitor ADT21 on IL-17 and IFN-γ levels (pro-inflammatory cytokines secreted from Th1 and Th17 T-cells), inventors isolated splenocyte from 30 week old NOD, control and ADT21 treated mice and incubated them with anti-CD3 (which mediates T-cell proliferation). The present inventors discovered a marked reduction in the levels of IL-17 and IFN-γ in cells obtained from treated mice (data not shown).

Figure 1A:
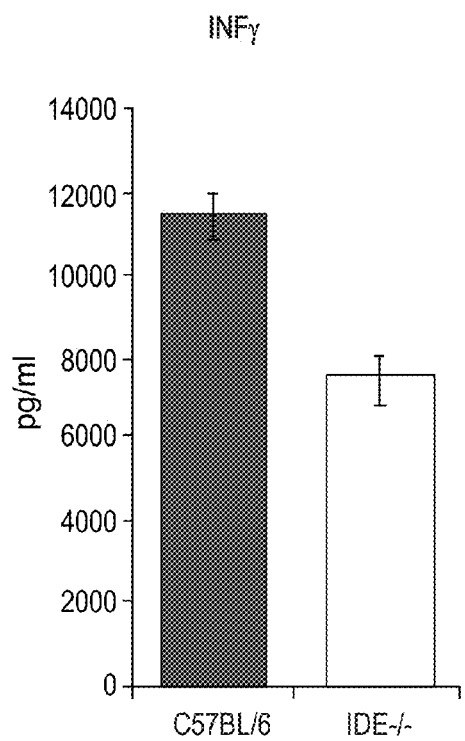
Figure 1B:
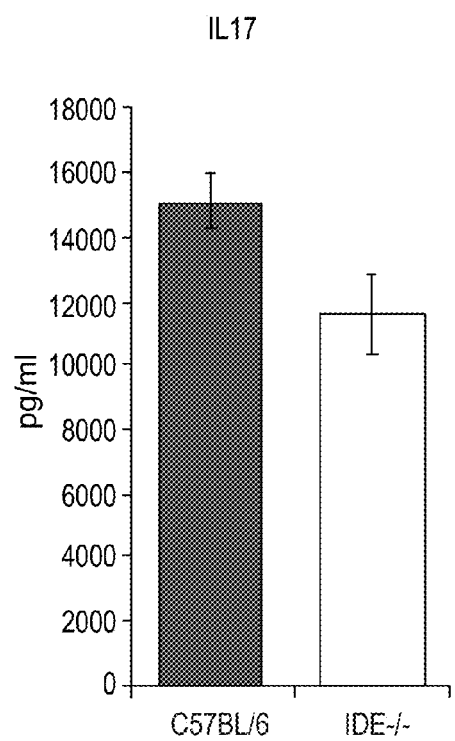
Figure 1C:
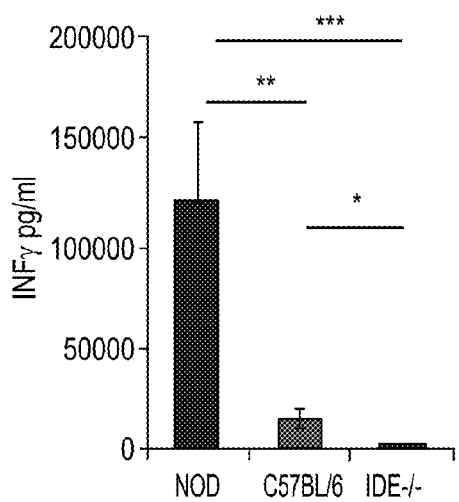
Figure 1D:
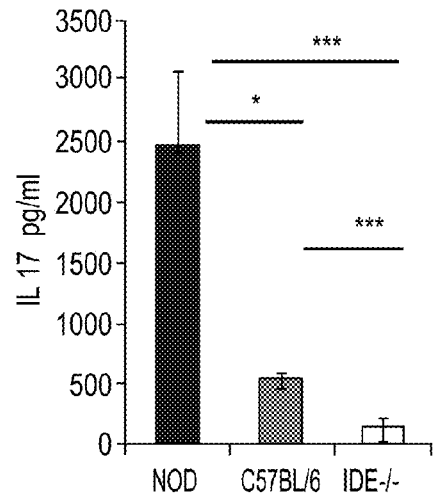
Figure 1E:
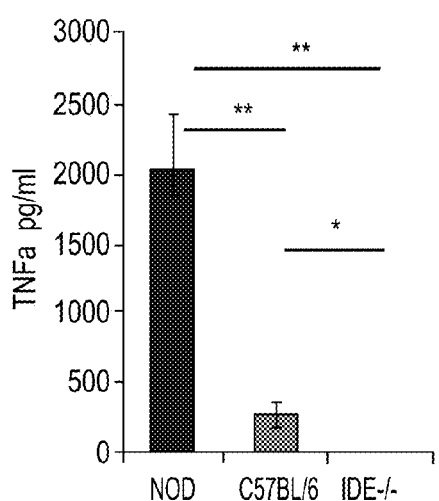
Figure 1F:
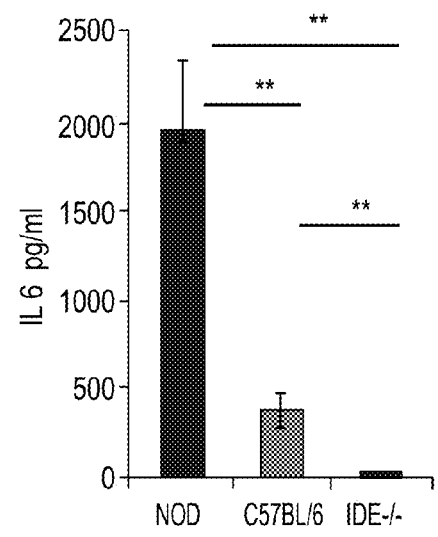

As previously discussed, there is a high tendency to obtain an autoimmune response to both islet and CNS antigen in diabetic and multiple sclerosis (MS) patients. Therefore, the present inventors investigated whether IDE modulates the autoimmune response against myelin antigens. Inventors immunized WT and IDE−/− mice, both on the background of C57BL/6 mice, with homogenized mouse spinal cord and measured the level of cytokines secreted from splenocytes. As illustrated in FIGS. 1A-B, the present inventors found a significant decrease in cytokine production that related to pro-inflammatory Th1 (IFN-γ) and Th17 (IL-17) in IDE−/− mice as compared to WT mice.

The present inventors have previously shown that MS progression in NOD mice is more severe compared to C57BL/6 EAE mice [Levy et al., (2010) Experimental Neurology 226 (2010) 148-158]. Therefore, inventors further investigated whether the reduction in pro-inflammatory cytokines in IDE−/− compared to WT mice related to immunization with the entire myelin antigen or small derivative such as MOG 35-55 (that is known to induce disease in C57BL/6 and NOD mice). In order to compare the pro-inflammatory reaction of the NOD, C57BL/6-WT and the IDE−/− mice, these mice were immunized with $MOG_{35-55}$, their spleens were isolated and then a measurement of the pro-inflammatory response was carried out as previously described [Levy et al., (2010) Experimental Neurology 226 (2010) 148-158]. As illustrated in FIGS. 1C-F, inventors found a significant decrease in pro-inflammatory cytokines in IDE−/− vs. C57BL/6 mice, which was related to a pro-inflammatory response of Th1 cells (IFN-γ, 81.5%; p<0.0001); Th17 cells (IL-17, 72%; p<0.0001); TNFα (76.5%; p<0.0001) and IL-6 (33.2%; p<0.01) as well as a remarkable increase in cytokines in NOD mice as compared to C57BL/6 mice: IFN-γ (759%; p=0.001); Th17 cells (IL-17, 352%; p=0.02); TNF-α (706%; p<0.01) and IL-6 (427%; p<0.01).

To measure the importance of IDE in the activation of the innate immunity, inventors incubated the splenocytes of naïve IDE−/− and WT (C57BL/6) mice in the presence of a known activator of the innate immune response, LPS. As illustrated in FIG. 2, inventors found a significant decrease in the levels of TNFα, a cytokine that measures macrophage and dendritic cell activation, in the IDE−/− mice as compare to WT mice.

IDE Dysfunction Reduces Levels of Pro-Inflammatory Cytokines Release

Following immunization of C57BL/6 mice with MOG35-55, CD4+ T-cells were isolated from spleen tissue. The isolated CD4+ T-cells were then co-cultured with antigen presenting cells (APC) isolated from non immunized mice or IDE−/− in the presence of MOG35-55 with or without an IDE inhibitor. As illustrated in FIGS. 3A-C, there was significant reduction in secretion of IFN-γ (FIG. 3A), IL-2 (FIG. 3B) and IL-6 (FIG. 3C) in the presence of an IDE inhibitor or with APCs obtained from IDE−/− mice vs. control mice.

To investigate the potential effect of IDE inhibitor on proliferation of specific MOG35-55 pro-inflammatory CD4+ T-cells, inventors isolated CD4+ T-cells of NOD $MOG_{35-55}$ immunized mice using magnetic beads and co-cultured them with non-immunized NOD APC in the presence of MOG and ADT21, an IDE blocker. Culture supernatants were collected after 48 hours, and quantitative ELISA was performed to measure the cytokine production. As illustrated in FIGS.

4A-B, a significant reduction in Th1 CD4+ T cell cytokine IFN-γ and in the APC IL-1γ pro-inflammatory cytokine was recorded in cell cultures that contained ADT21.

Inventors next compared the IDE expression levels on macrophages following incubation with IFN-γ, a known macrophage and microglia activator that plays a role in the development of MS. Using western-blot analysis, inventors found a significant increase in IDE expression on microglia cells (FIG. 5A) in parallel with increase in nitric oxide (NO, FIG. 5B) that link to macrophage/microglia activity and may be operative in neurodegenerative diseases such as MS.

Treatment with IDE Inhibitor Significantly Reduces Disease Progression in MS Animal Model Inventors further investigated whether down-regulation of IDE using an IDE inhibitor can reduce splenocyte activation in vivo. Inventors immunized 8-week-old C57BL/6 mice with MOG35-55 in CFA. The mice were nasally administered with an IDE inhibitor, ADT21, starting a day before the immunization and during the following 11 days. PBS treated mice served as control. At the end of treatment, the splenocytes were removed and cultured, and the level of cytokines was measured using ELISA. As illustrated in FIGS. 6A-D, inventors found a significant reduction in cytokines that to were related to the pro-inflammatory response of Th1 cells (IFN-γ) (79.6%) and of Th17 cells (IL-17, 66.1%); TNF-α (42.2%) and IL-6 (37.7%) in ADT21-treated mice as compared to control C57BL/6 mice. These results suggest that IDE may modulate an autoimmune response against myelin antigen and therefore should be an important target for further research for its role in disease progression in MS.

Inventors further investigate the effect of IDE inhibitor in ameliorating autoimmune disease in vivo in a MS animal model. EAE was induced in 10-week-old NOD mice through immunizing with MOG35-55 in CFA. 18 days after EAE induction, mice received every other day a nasal IDE inhibitor treatment. As illustrated in FIG. 7, the present inventors discovered that the clinical score was significantly reduced in the ADT21-treated mice as compared to PBS treated mice. These results emphasize the role of IDE inhibitors as therapeutic application in MS.

Example 2

Effect of the Peptides of the Present Invention on Alzheimer's Disease

Materials and Experimental Procedures
Animals
8-week-old APP/PSI mice were used as previously described (Oakley et al 2006, J Neurosci 26: 10129-10140). Mice were treated with either ADT21 (1.07 μg/mouse) or PBS every other day for 4 months.

Behavioral Tests

Contextual fear conditioning was tested as described previously (Carlos A. et al., 2005) Mice were placed within the conditioning chamber (Coulbourn Instruments, Allentown, Pa.) (7"W×7"D×12"H) for 3 min before the onset of the unconditioned stimulus (US; footshock; 1 s/1 mA) through the cage grid floor (Model H10-11M-TC-SF) from a Coulbourn Instruments shocker (Model H13-15). Activation was detected via a camera above the cage (ACT-VP-01) with a special algorithm for motion detection, to allow them to develop a representation of the context via exploration. After the shock, mice were left in the chamber for 2 min (immediate freezing) and returned to their home cages. 24 hours after the training session, the mice were again placed in the chamber and tested for 4 min without any footshocks. The chamber was isolated in a quiet environment using the noise sealed box (H10-24T Coulbourn Instruments). Freezing response was scored by using the FreezeFrame automated system (Coulbourn Instruments). Furthermore, mice were daily monitored for body weight, eating habits, tail tone and mobility.

Measurement of Insulin Levels 2 months old APP/PS1 male mice were treated intranasally with either ADT-21 (1.07 μg/mouse) or PBS for 4 month every two days. At the age of 6 months, mice were sacrificed and their blood was collected. Insulin (ug/L) serum levels were determined using Ultrasensitive mouse Insulin ELISA kit (Mercodia).

Immuno-Histological Analysis 2 month old APP/PS1 mice were treated nasally for 4 months, every two days with ADT21 (1.07 μg/mouse) or with placebo (PBS treated mice). The brains were perfused and freshly frozen for 72 hours. 14 μm coronal brain sections were prepared from 6-month-old APP/PS1 mice using cryostat. The slices were then stained at Bregma −1.58 mm with Congo Red staining [Sigma-C6767].

Results 8-week-old APP mice were treated with either ADT21 (1.07 μg/mouse) or PBS every other day for 4 months. The ADT21-treated animals exhibited no changes in their behavior, as measured by body weight, eating habits, tail tone, or mobility, that indicated toxicity. In order to investigate whether nasal ADT21 administration ameliorated disease progression and improves cognition, inventors used contextual fear conditioning test. Inventors discovered that while APP Tg mice had significant deficient in memory at the age of 6 months vs. control, ADT21 treatment improved cognitive behavior in the APP/PS1 mouse model FIG. 8.

In order to confirm that the difference between the treated group to the control group was related to higher insulin in the blood, inventors bled the animals at the age of 6 months and tested the level of insulin in the serum. As illustrated in FIG. 9, inventors discovered that ADT21 treatment yielded an increase of about 700% in the level of insulin as compared to control APP Tg mice (p=0.0339).

Following the behavioral assays, the animals were sacrificed for immuno-histological analysis of amyloid load. When stained with Congo red, a specific amyloid-binding dye, a reduction in amyloid plaque of 65% was observed (P=0.034) (FIGS. 10A-C).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a disease selected from the group consisting of an Alzheimer's disease, Parkinson's disease and Multiple Sclerosis, the method comprising administering to a subject in need thereof a therapeutically effective amount of an insulin degrading enzyme (IDE) peptide inhibitor, wherein said IDE peptide inhibitor is selected from the group consisting of SEQ ID NO: 6, SEQ ID NO: 17, SEQ ID NO: 18, SEQ ID NO: 19, SEQ ID NO: 20, thereby treating the disease in the subject.

2. The method of claim 1, wherein said IDE peptide inhibitor is as set forth in SEQ ID NO: 6.

3. The method of claim 1, wherein the subject is a human subject.

4. The method of claim 1, wherein said IDE inhibitor is attached to a cell penetrating peptide.

5. The method of claim 1, wherein said IDE inhibitor is conjugated to mannitol, a lipid, cholesterol or a transport peptide for passage through the blood brain barrier.

6. A method for treating Alzheimer's disease in a subject in need thereof, the method comprising administering to the subject a therapeutically effective amount of an insulin degrading enzyme (IDE) peptide inhibitor as set forth in SEQ ID NO: 6, thereby treating the Alzheimer's disease in the subject.

* * * * *

SEQUENCE LISTING

<160> NUMBER OF SEQ ID NOS: 82

<210> SEQ ID NO 1
<211> LENGTH: 10
<212> TYPE: PRT
<213> ORGANISM: Artificial sequence
<220> FEATURE:
<223> OTHER INFORMATION: ADT-1 IDE inhibitory peptide

<400> SEQUENCE: 1

Val Leu Arg Tyr Asp Asp Phe His Thr Asp
1               5                   10

<210> SEQ ID NO 2
<211> LENGTH: 10
<212> TYPE: PRT
<213> ORGANISM: Artificial sequence
<220> FEATURE:
<223> OTHER INFORMATION: ADT-2 IDE inhibitory peptide

<400> SEQUENCE: 2

Glu Ala Leu Tyr Asp Asp Leu Val Cys Gly
1               5                   10

<210> SEQ ID NO 3
<211> LENGTH: 13
<212> TYPE: PRT
<213> ORGANISM: Artificial sequence
<220> FEATURE:
<223> OTHER INFORMATION: ADT-3 IDE inhibitory peptide

<400> SEQUENCE: 3

Leu Ala Asn Phe Asp Asp Leu Val His Ser Ser Asn Asn
1               5                   10

<210> SEQ ID NO 4
<211> LENGTH: 9
<212> TYPE: PRT
<213> ORGANISM: Artificial sequence
<220> FEATURE:
<223> OTHER INFORMATION: ADT-4 IDE inhibitory peptide

<400> SEQUENCE: 4

Phe Val Gln Trp Asp Asp Leu Met Asn
1               5

<210> SEQ ID NO 5
<211> LENGTH: 10
<212> TYPE: PRT
<213> ORGANISM: Artificial sequence
<220> FEATURE:
<223> OTHER INFORMATION: ADT-5 IDE inhibitory peptide

<400> SEQUENCE: 5

Lys Leu Val Phe Asp Asp Phe Ala Glu Asp
1               5                   10

<210> SEQ ID NO 6
<211> LENGTH: 20
<212> TYPE: PRT
<213> ORGANISM: Artificial sequence
<220> FEATURE:
<223> OTHER INFORMATION: ADT-21 IDE inhibitory peptide -continued

```
<400> SEQUENCE: 6

Ile Thr Asn Pro Gly Ser Gly Gly Ser Ser Val Leu Arg Tyr Asp Asp
1               5                   10                  15

Phe His Thr Asp
            20

<210> SEQ ID NO 7
<211> LENGTH: 20
<212> TYPE: PRT
<213> ORGANISM: Artificial sequence
<220> FEATURE:
<223> OTHER INFORMATION: ADT-22 IDE inhibitory peptide

<400> SEQUENCE: 7

Phe Val Asn Gln Gly Ser Gly Gly Ser Ser Glu Ala Leu Tyr Asp Asp
1               5                   10                  15

Leu Val Cys Gly
            20

<210> SEQ ID NO 8
<211> LENGTH: 23
<212> TYPE: PRT
<213> ORGANISM: Artificial sequence
<220> FEATURE:
<223> OTHER INFORMATION: ADT-23 IDE inhibitory peptide

<400> SEQUENCE: 8

Lys Cys Asn Thr Gly Ser Gly Gly Ser Ser Leu Ala Asn Phe Asp Asp
1               5                   10                  15

Leu Val His Ser Ser Asn Asn
            20

<210> SEQ ID NO 9
<211> LENGTH: 19
<212> TYPE: PRT
<213> ORGANISM: Artificial sequence
<220> FEATURE:
<223> OTHER INFORMATION: ADT-24 IDE inhibitory peptide

<400> SEQUENCE: 9

His Ser Gln Gly Gly Ser Gly Gly Ser Ser Phe Val Gln Trp Asp Asp
1               5                   10                  15

Leu Met Asn

<210> SEQ ID NO 10
<211> LENGTH: 20
<212> TYPE: PRT
<213> ORGANISM: Artificial sequence
<220> FEATURE:
<223> OTHER INFORMATION: ADT-25 IDE inhibitory peptide

<400> SEQUENCE: 10

Asp Ala Glu Phe Gly Ser Gly Gly Ser Ser Lys Leu Val Phe Asp Asp
1               5                   10                  15

Phe Ala Glu Asp
            20

<210> SEQ ID NO 11
<211> LENGTH: 2
<212> TYPE: PRT
<213> ORGANISM: Artificial sequence
<220> FEATURE:
<223> OTHER INFORMATION: ADT-31 IDE inhibitory peptide
```

```
<400> SEQUENCE: 11

Asp Asp
1

<210> SEQ ID NO 12
<211> LENGTH: 10
<212> TYPE: PRT
<213> ORGANISM: Artificial sequence
<220> FEATURE:
<223> OTHER INFORMATION: ADT-32 IDE inhibitory peptide

<400> SEQUENCE: 12

Asp Asp Glu Ala Leu Tyr Leu Val Cys Gly
1               5                   10

<210> SEQ ID NO 13
<211> LENGTH: 10
<212> TYPE: PRT
<213> ORGANISM: Artificial sequence
<220> FEATURE:
<223> OTHER INFORMATION: ADT-33 IDE inhibitory peptide

<400> SEQUENCE: 13

Glu Ala Leu Tyr Asn Asn Leu Val Cys Gly
1               5                   10

<210> SEQ ID NO 14
<211> LENGTH: 10
<212> TYPE: PRT
<213> ORGANISM: Artificial sequence
<220> FEATURE:
<223> OTHER INFORMATION: ADT-34 IDE inhibitory peptide

<400> SEQUENCE: 14

Glu Ala Leu Tyr Ala Ala Leu Val Cys Gly
1               5                   10

<210> SEQ ID NO 15
<211> LENGTH: 10
<212> TYPE: PRT
<213> ORGANISM: Artificial sequence
<220> FEATURE:
<223> OTHER INFORMATION: ADT-35 IDE inhibitory peptide

<400> SEQUENCE: 15

Glu Ala Leu Tyr Phe Phe Leu Val Cys Gly
1               5                   10

<210> SEQ ID NO 16
<211> LENGTH: 10
<212> TYPE: PRT
<213> ORGANISM: Artificial sequence
<220> FEATURE:
<223> OTHER INFORMATION: ADT-36 IDE inhibitory peptide

<400> SEQUENCE: 16

Glu Ala Leu Tyr Glu Glu Leu Val Cys Gly
1               5                   10

<210> SEQ ID NO 17
<211> LENGTH: 20
<212> TYPE: PRT
<213> ORGANISM: Artificial sequence
<220> FEATURE:
<223> OTHER INFORMATION: ADT-41 IDE inhibitory peptide

<400> SEQUENCE: 17
```

```
Ile Thr Asn Pro Gly Ser Gly Gly Ser Glu Ala Leu Tyr Asp Asp
1               5                   10                  15

Leu Val Cys Gly
            20

<210> SEQ ID NO 18
<211> LENGTH: 23
<212> TYPE: PRT
<213> ORGANISM: Artificial sequence
<220> FEATURE:
<223> OTHER INFORMATION: ADT-42 IDE inhibitory peptide

<400> SEQUENCE: 18

Ile Thr Asn Pro Gly Ser Gly Gly Ser Ser Leu Ala Asn Phe Asp Asp
1               5                   10                  15

Leu Val His Ser Ser Asn Asn
            20

<210> SEQ ID NO 19
<211> LENGTH: 19
<212> TYPE: PRT
<213> ORGANISM: Artificial sequence
<220> FEATURE:
<223> OTHER INFORMATION: ADT-43 IDE inhibitory peptide

<400> SEQUENCE: 19

Ile Thr Asn Pro Gly Ser Gly Gly Ser Ser Phe Val Gln Trp Asp Asp
1               5                   10                  15

Leu Met Asn

<210> SEQ ID NO 20
<211> LENGTH: 20
<212> TYPE: PRT
<213> ORGANISM: Artificial sequence
<220> FEATURE:
<223> OTHER INFORMATION: ADT-44 IDE inhibitory peptide

<400> SEQUENCE: 20

Ile Thr Asn Pro Gly Ser Gly Gly Ser Ser Lys Leu Val Phe Asp Asp
1               5                   10                  15

Phe Ala Glu Asp
            20

<210> SEQ ID NO 21
<211> LENGTH: 20
<212> TYPE: PRT
<213> ORGANISM: Artificial sequence
<220> FEATURE:
<223> OTHER INFORMATION: ADT-51 IDE inhibitory peptide

<400> SEQUENCE: 21

Phe Val Asn Gln Gly Ser Gly Gly Ser Ser Val Leu Arg Tyr Asp Asp
1               5                   10                  15

Phe His Thr Asp
            20

<210> SEQ ID NO 22
<211> LENGTH: 23
<212> TYPE: PRT
<213> ORGANISM: Artificial sequence
<220> FEATURE:
<223> OTHER INFORMATION: ADT-52 IDE inhibitory peptide

<400> SEQUENCE: 22
```

```
Phe Val Asn Gln Gly Ser Gly Gly Ser Ser Leu Ala Asn Phe Asp Asp
1               5                   10                  15

Leu Val His Ser Ser Asn Asn
            20

<210> SEQ ID NO 23
<211> LENGTH: 19
<212> TYPE: PRT
<213> ORGANISM: Artificial sequence
<220> FEATURE:
<223> OTHER INFORMATION: ADT-53 IDE inhibitory peptide

<400> SEQUENCE: 23

Phe Val Asn Gln Gly Ser Gly Gly Ser Ser Phe Val Gln Trp Asp Asp
1               5                   10                  15

Leu Met Asn

<210> SEQ ID NO 24
<211> LENGTH: 20
<212> TYPE: PRT
<213> ORGANISM: Artificial sequence
<220> FEATURE:
<223> OTHER INFORMATION: ADT-54 IDE inhibitory peptide

<400> SEQUENCE: 24

Phe Val Asn Gln Gly Ser Gly Gly Ser Ser Lys Leu Val Phe Asp Asp
1               5                   10                  15

Phe Ala Glu Asp
            20

<210> SEQ ID NO 25
<211> LENGTH: 20
<212> TYPE: PRT
<213> ORGANISM: Artificial sequence
<220> FEATURE:
<223> OTHER INFORMATION: ADT-61 IDE inhibitory peptide

<400> SEQUENCE: 25

Lys Cys Asn Thr Gly Ser Gly Gly Ser Ser Val Leu Arg Tyr Asp Asp
1               5                   10                  15

Phe His Thr Asp
            20

<210> SEQ ID NO 26
<211> LENGTH: 20
<212> TYPE: PRT
<213> ORGANISM: Artificial sequence
<220> FEATURE:
<223> OTHER INFORMATION: ADT-62 IDE inhibitory peptide

<400> SEQUENCE: 26

Lys Cys Asn Thr Gly Ser Gly Gly Ser Ser Glu Ala Leu Tyr Asp Asp
1               5                   10                  15

Leu Val Cys Gly
            20

<210> SEQ ID NO 27
<211> LENGTH: 19
<212> TYPE: PRT
<213> ORGANISM: Artificial sequence
<220> FEATURE:
<223> OTHER INFORMATION: ADT-63 IDE inhibitory peptide

<400> SEQUENCE: 27
```

```
Lys Cys Asn Thr Gly Ser Gly Gly Ser Phe Val Gln Trp Asp Asp
1               5                   10                  15

Leu Met Asn

<210> SEQ ID NO 28
<211> LENGTH: 20
<212> TYPE: PRT
<213> ORGANISM: Artificial sequence
<220> FEATURE:
<223> OTHER INFORMATION: ADT-64 IDE inhibitory peptide

<400> SEQUENCE: 28

Lys Cys Asn Thr Gly Ser Gly Gly Ser Lys Leu Val Phe Asp Asp
1               5                   10                  15

Phe Ala Glu Asp
            20

<210> SEQ ID NO 29
<211> LENGTH: 20
<212> TYPE: PRT
<213> ORGANISM: Artificial sequence
<220> FEATURE:
<223> OTHER INFORMATION: ADT-71 IDE inhibitory peptide

<400> SEQUENCE: 29

His Ser Gln Gly Gly Ser Gly Gly Ser Ser Val Leu Arg Tyr Asp Asp
1               5                   10                  15

Phe His Thr Asp
            20

<210> SEQ ID NO 30
<211> LENGTH: 20
<212> TYPE: PRT
<213> ORGANISM: Artificial sequence
<220> FEATURE:
<223> OTHER INFORMATION: ADT-72 IDE inhibitory peptide

<400> SEQUENCE: 30

His Ser Gln Gly Gly Ser Gly Gly Ser Ser Glu Ala Leu Tyr Asp Asp
1               5                   10                  15

Leu Val Cys Gly
            20

<210> SEQ ID NO 31
<211> LENGTH: 23
<212> TYPE: PRT
<213> ORGANISM: Artificial sequence
<220> FEATURE:
<223> OTHER INFORMATION: ADT-73 IDE inhibitory peptide

<400> SEQUENCE: 31

His Ser Gln Gly Gly Ser Gly Gly Ser Ser Leu Ala Asn Phe Asp Asp
1               5                   10                  15

Leu Val His Ser Ser Asn Asn
            20

<210> SEQ ID NO 32
<211> LENGTH: 20
<212> TYPE: PRT
<213> ORGANISM: Artificial sequence
<220> FEATURE:
<223> OTHER INFORMATION: ADT-74 IDE inhibitory peptide

<400> SEQUENCE: 32
```

```
His Ser Gln Gly Gly Ser Gly Gly Ser Lys Leu Val Phe Asp Asp
1               5                   10                  15

Phe Ala Glu Asp
            20

<210> SEQ ID NO 33
<211> LENGTH: 20
<212> TYPE: PRT
<213> ORGANISM: Artificial sequence
<220> FEATURE:
<223> OTHER INFORMATION: ADT-81 IDE inhibitory peptide

<400> SEQUENCE: 33

Asp Ala Glu Phe Gly Ser Gly Gly Ser Val Leu Arg Tyr Asp Asp
1               5                   10                  15

Phe His Thr Asp
            20

<210> SEQ ID NO 34
<211> LENGTH: 20
<212> TYPE: PRT
<213> ORGANISM: Artificial sequence
<220> FEATURE:
<223> OTHER INFORMATION: ADT-82 IDE inhibitory peptide

<400> SEQUENCE: 34

Asp Ala Glu Phe Gly Ser Gly Gly Ser Glu Ala Leu Tyr Asp Asp
1               5                   10                  15

Leu Val Cys Gly
            20

<210> SEQ ID NO 35
<211> LENGTH: 23
<212> TYPE: PRT
<213> ORGANISM: Artificial sequence
<220> FEATURE:
<223> OTHER INFORMATION: ADT-83 IDE inhibitory peptide

<400> SEQUENCE: 35

Asp Ala Glu Phe Gly Ser Gly Gly Ser Leu Ala Asn Phe Asp Asp
1               5                   10                  15

Leu Val His Ser Ser Asn Asn
            20

<210> SEQ ID NO 36
<211> LENGTH: 19
<212> TYPE: PRT
<213> ORGANISM: Artificial sequence
<220> FEATURE:
<223> OTHER INFORMATION: ADT-84 IDE inhibitory peptide

<400> SEQUENCE: 36

Asp Ala Glu Phe Gly Ser Gly Gly Ser Phe Val Gln Trp Asp Asp
1               5                   10                  15

Leu Met Asn

<210> SEQ ID NO 37
<211> LENGTH: 30
<212> TYPE: DNA
<213> ORGANISM: Artificial sequence
<220> FEATURE:
<223> OTHER INFORMATION: Exemplary nucleotide sequence encoding ADT-1
      IDE peptide
```

```
<400> SEQUENCE: 37
gtgctgcgct atgatgattt tcataccgat                                   30

<210> SEQ ID NO 38
<211> LENGTH: 30
<212> TYPE: DNA
<213> ORGANISM: Artificial sequence
<220> FEATURE:
<223> OTHER INFORMATION: Exemplary nucleotide sequence encoding ADT-2
      IDE peptide

<400> SEQUENCE: 38
gaagcgctgt atgatgatct ggtgtgcggc                                   30

<210> SEQ ID NO 39
<211> LENGTH: 39
<212> TYPE: DNA
<213> ORGANISM: Artificial sequence
<220> FEATURE:
<223> OTHER INFORMATION: Exemplary nucleotide sequence encoding ADT-3
      IDE peptide

<400> SEQUENCE: 39
ctggcgaact tgatgatct ggtgcatagc agcaacaac                          39

<210> SEQ ID NO 40
<211> LENGTH: 27
<212> TYPE: DNA
<213> ORGANISM: Artificial sequence
<220> FEATURE:
<223> OTHER INFORMATION: Exemplary nucleotide sequence encoding ADT-4
      IDE peptide

<400> SEQUENCE: 40
tttgtgcagt gggatgatct gatgaac                                      27

<210> SEQ ID NO 41
<211> LENGTH: 30
<212> TYPE: DNA
<213> ORGANISM: Artificial sequence
<220> FEATURE:
<223> OTHER INFORMATION: Exemplary nucleotide sequence encoding ADT-5
      IDE peptide

<400> SEQUENCE: 41
aaactggtgt tgatgatttt tgcggaagat                                   30

<210> SEQ ID NO 42
<211> LENGTH: 60
<212> TYPE: DNA
<213> ORGANISM: Artificial sequence
<220> FEATURE:
<223> OTHER INFORMATION: Exemplary nucleotide sequence encoding ADT-21
      IDE peptide

<400> SEQUENCE: 42
attaccaacc cgggcagcgg cggcagcagc gtgctgcgct atgatgattt tcataccgat  60

<210> SEQ ID NO 43
<211> LENGTH: 60
<212> TYPE: DNA
<213> ORGANISM: Artificial sequence
<220> FEATURE:
<223> OTHER INFORMATION: Exemplary nucleotide sequence encoding ADT-22
      IDE peptide

<400> SEQUENCE: 43
```

-continued

```
tttgtgaacc agggcagcgg cggcagcagc gaagcgctgt atgatgatct ggtgtgcggc    60
```

<210> SEQ ID NO 44
<211> LENGTH: 69
<212> TYPE: DNA
<213> ORGANISM: Artificial sequence
<220> FEATURE:
<223> OTHER INFORMATION: Exemplary nucleotide sequence encoding ADT-23
       IDE peptide

<400> SEQUENCE: 44

```
aaatgcaaca ccggcagcgg cggcagcagc ctggcgaact tgatgatct ggtgcatagc    60 agcaacaac                                                            69
```

<210> SEQ ID NO 45
<211> LENGTH: 57
<212> TYPE: DNA
<213> ORGANISM: Artificial sequence
<220> FEATURE:
<223> OTHER INFORMATION: Exemplary nucleotide sequence encoding ADT-24
       IDE peptide

<400> SEQUENCE: 45

```
catagccagg gcggcagcgg cggcagcagc tttgtgcagt gggatgatct gatgaac      57
```

<210> SEQ ID NO 46
<211> LENGTH: 60
<212> TYPE: DNA
<213> ORGANISM: Artificial sequence
<220> FEATURE:
<223> OTHER INFORMATION: Exemplary nucleotide sequence encoding ADT-25
       IDE peptide

<400> SEQUENCE: 46

```
gatgcggaat tggcagcgg cggcagcagc aaactggtgt tgatgattt tgcggaagat    60
```

<210> SEQ ID NO 47
<211> LENGTH: 6
<212> TYPE: DNA
<213> ORGANISM: Artificial sequence
<220> FEATURE:
<223> OTHER INFORMATION: Exemplary nucleotide sequence encoding ADT-31
       IDE peptide

<400> SEQUENCE: 47

```
gatgat                                                               6
```

<210> SEQ ID NO 48
<211> LENGTH: 30
<212> TYPE: DNA
<213> ORGANISM: Artificial sequence
<220> FEATURE:
<223> OTHER INFORMATION: Exemplary nucleotide sequence encoding ADT-32
       IDE peptide

<400> SEQUENCE: 48

```
gatgatgaag cgctgtatct ggtgtgcggc                                     30
```

<210> SEQ ID NO 49
<211> LENGTH: 30
<212> TYPE: DNA
<213> ORGANISM: Artificial sequence
<220> FEATURE:
<223> OTHER INFORMATION: Exemplary nucleotide sequence encoding ADT-33
       IDE peptide

<400> SEQUENCE: 49
gaagcgctgt ataacaacct ggtgtgcggc                               30

<210> SEQ ID NO 50
<211> LENGTH: 30
<212> TYPE: DNA
<213> ORGANISM: Artificial sequence
<220> FEATURE:
<223> OTHER INFORMATION: Exemplary nucleotide sequence encoding ADT-34
      IDE peptide

<400> SEQUENCE: 50
gaagcgctgt atgcggcgct ggtgtgcggc                               30

<210> SEQ ID NO 51
<211> LENGTH: 30
<212> TYPE: DNA
<213> ORGANISM: Artificial sequence
<220> FEATURE:
<223> OTHER INFORMATION: Exemplary nucleotide sequence encoding ADT-35
      IDE peptide

<400> SEQUENCE: 51
gaagcgctgt atttttttct ggtgtgcggc                               30

<210> SEQ ID NO 52
<211> LENGTH: 60
<212> TYPE: DNA
<213> ORGANISM: Artificial sequence
<220> FEATURE:
<223> OTHER INFORMATION: Exemplary nucleotide sequence encoding ADT-41
      IDE peptide

<400> SEQUENCE: 52
attaccaacc cgggcagcgg cggcagcagc gaagcgctgt atgatgatct ggtgtgcggc   60

<210> SEQ ID NO 53
<211> LENGTH: 69
<212> TYPE: DNA
<213> ORGANISM: Artificial sequence
<220> FEATURE:
<223> OTHER INFORMATION: Exemplary nucleotide sequence encoding ADT-42
      IDE peptide

<400> SEQUENCE: 53
attaccaacc cgggcagcgg cggcagcagc ctggcgaact ttgatgatct ggtgcatagc   60
agcaacaac                                                         69

<210> SEQ ID NO 54
<211> LENGTH: 57
<212> TYPE: DNA
<213> ORGANISM: Artificial sequence
<220> FEATURE:
<223> OTHER INFORMATION: Exemplary nucleotide sequence encoding ADT-43
      IDE peptide

<400> SEQUENCE: 54
attaccaacc cgggcagcgg cggcagcagc tttgtgcagt gggatgatct gatgaac      57

<210> SEQ ID NO 55
<211> LENGTH: 60
<212> TYPE: DNA
<213> ORGANISM: Artificial sequence
<220> FEATURE:
<223> OTHER INFORMATION: Exemplary nucleotide sequence encoding ADT-44
      IDE peptide

```
<400> SEQUENCE: 55
attaccaacc cgggcagcgg cggcagcagc aaactggtgt ttgatgattt tgcggaagat    60

<210> SEQ ID NO 56
<211> LENGTH: 60
<212> TYPE: DNA
<213> ORGANISM: Artificial sequence
<220> FEATURE:
<223> OTHER INFORMATION: Exemplary nucleotide sequence encoding ADT-51
      IDE peptide

<400> SEQUENCE: 56
tttgtgaacc agggcagcgg cggcagcagc gtgctgcgct atgatgattt tcataccgat    60

<210> SEQ ID NO 57
<211> LENGTH: 69
<212> TYPE: DNA
<213> ORGANISM: Artificial sequence
<220> FEATURE:
<223> OTHER INFORMATION: Exemplary nucleotide sequence encoding ADT-52
      IDE peptide

<400> SEQUENCE: 57
tttgtgaacc agggcagcgg cggcagcagc ctggcgaact ttgatgatct ggtgcatagc    60
agcaacaac                                                            69

<210> SEQ ID NO 58
<211> LENGTH: 57
<212> TYPE: DNA
<213> ORGANISM: Artificial sequence
<220> FEATURE:
<223> OTHER INFORMATION: Exemplary nucleotide sequence encoding ADT-53
      IDE peptide

<400> SEQUENCE: 58
tttgtgaacc agggcagcgg cggcagcagc tttgtgcagt gggatgatct gatgaac       57

<210> SEQ ID NO 59
<211> LENGTH: 60
<212> TYPE: DNA
<213> ORGANISM: Artificial sequence
<220> FEATURE:
<223> OTHER INFORMATION: Exemplary nucleotide sequence encoding ADT-54
      IDE peptide

<400> SEQUENCE: 59
tttgtgaacc agggcagcgg cggcagcagc aaactggtgt ttgatgattt tgcggaagat    60

<210> SEQ ID NO 60
<211> LENGTH: 60
<212> TYPE: DNA
<213> ORGANISM: Artificial sequence
<220> FEATURE:
<223> OTHER INFORMATION: Exemplary nucleotide sequence encoding ADT-61
      IDE peptide

<400> SEQUENCE: 60
aaatgcaaca ccggcagcgg cggcagcagc gtgctgcgct atgatgattt tcataccgat    60

<210> SEQ ID NO 61
<211> LENGTH: 60
<212> TYPE: DNA
<213> ORGANISM: Artificial sequence
<220> FEATURE:
<223> OTHER INFORMATION: Exemplary nucleotide sequence encoding ADT-62
```

```
            IDE peptide

<400> SEQUENCE: 61
aaatgcaaca ccggcagcgg cggcagcagc gaagcgctgt atgatgatct ggtgtgcggc      60

<210> SEQ ID NO 62
<211> LENGTH: 57
<212> TYPE: DNA
<213> ORGANISM: Artificial sequence
<220> FEATURE:
<223> OTHER INFORMATION: Exemplary nucleotide sequence encoding ADT-63
      IDE peptide

<400> SEQUENCE: 62
aaatgcaaca ccggcagcgg cggcagcagc tttgtgcagt gggatgatct gatgaac         57

<210> SEQ ID NO 63
<211> LENGTH: 60
<212> TYPE: DNA
<213> ORGANISM: Artificial sequence
<220> FEATURE:
<223> OTHER INFORMATION: Exemplary nucleotide sequence encoding ADT-64
      IDE peptide

<400> SEQUENCE: 63
aaatgcaaca ccggcagcgg cggcagcagc aaactggtgt tgatgatttt tgcggaagat      60

<210> SEQ ID NO 64
<211> LENGTH: 60
<212> TYPE: DNA
<213> ORGANISM: Artificial sequence
<220> FEATURE:
<223> OTHER INFORMATION: Exemplary nucleotide sequence encoding ADT-71
      IDE peptide

<400> SEQUENCE: 64
catagccagg gcggcagcgg cggcagcagc gtgctgcgct atgatgattt tcataccgat      60

<210> SEQ ID NO 65
<211> LENGTH: 60
<212> TYPE: DNA
<213> ORGANISM: Artificial sequence
<220> FEATURE:
<223> OTHER INFORMATION: Exemplary nucleotide sequence encoding ADT-72
      IDE peptide

<400> SEQUENCE: 65
catagccagg gcggcagcgg cggcagcagc gaagcgctgt atgatgatct ggtgtgcggc      60

<210> SEQ ID NO 66
<211> LENGTH: 69
<212> TYPE: DNA
<213> ORGANISM: Artificial sequence
<220> FEATURE:
<223> OTHER INFORMATION: Exemplary nucleotide sequence encoding ADT-73
      IDE peptide

<400> SEQUENCE: 66
catagccagg gcggcagcgg cggcagcagc ctggcgaact tgatgatct ggtgcatagc       60 agcaacaac                                                              69

<210> SEQ ID NO 67
<211> LENGTH: 60
<212> TYPE: DNA
<213> ORGANISM: Artificial sequence
<220> FEATURE:
```

<223> OTHER INFORMATION: Exemplary nucleotide sequence encoding ADT-74
      IDE peptide

<400> SEQUENCE: 67
catagccagg gcggcagcgg cggcagcagc aaactggtgt ttgatgattt tgcggaagat    60

<210> SEQ ID NO 68
<211> LENGTH: 60
<212> TYPE: DNA
<213> ORGANISM: Artificial sequence
<220> FEATURE:
<223> OTHER INFORMATION: Exemplary nucleotide sequence encoding ADT-81
      IDE peptide

<400> SEQUENCE: 68
gatgcggaat tggcagcgg cggcagcagc gtgctgcgct atgatgattt tcataccgat    60

<210> SEQ ID NO 69
<211> LENGTH: 60
<212> TYPE: DNA
<213> ORGANISM: Artificial sequence
<220> FEATURE:
<223> OTHER INFORMATION: Exemplary nucleotide sequence encoding ADT-82
      IDE peptide

<400> SEQUENCE: 69
gatgcggaat tggcagcgg cggcagcagc gaagcgctgt atgatgatct ggtgtgcggc    60

<210> SEQ ID NO 70
<211> LENGTH: 69
<212> TYPE: DNA
<213> ORGANISM: Artificial sequence
<220> FEATURE:
<223> OTHER INFORMATION: Exemplary nucleotide sequence encoding ADT-83
      IDE peptide

<400> SEQUENCE: 70
gatgcggaat tggcagcgg cggcagcagc ctggcgaact ttgatgatct ggtgcatagc    60
agcaacaac                                                            69

<210> SEQ ID NO 71
<211> LENGTH: 57
<212> TYPE: DNA
<213> ORGANISM: Artificial sequence
<220> FEATURE:
<223> OTHER INFORMATION: Exemplary nucleotide sequence encoding ADT-84
      IDE peptide

<400> SEQUENCE: 71
gatgcggaat tggcagcgg cggcagcagc tttgtgcagt gggatgatct gatgaac       57

<210> SEQ ID NO 72
<211> LENGTH: 4
<212> TYPE: PRT
<213> ORGANISM: Artificial sequence
<220> FEATURE:
<223> OTHER INFORMATION: A peptide sequence derived from Insulin B chain
      (25-28) N'

<400> SEQUENCE: 72

Phe Val Asn Gln
1

<210> SEQ ID NO 73
<211> LENGTH: 4
<212> TYPE: PRT

```
<213> ORGANISM: Artificial sequence
<220> FEATURE:
<223> OTHER INFORMATION: A peptide sequence derived from Amylin (34-37)
      N'

<400> SEQUENCE: 73

Lys Cys Asn Thr
1

<210> SEQ ID NO 74
<211> LENGTH: 4
<212> TYPE: PRT
<213> ORGANISM: Artificial sequence
<220> FEATURE:
<223> OTHER INFORMATION: A peptide sequence derived from Glucagon
      (53-56) N'

<400> SEQUENCE: 74

His Ser Gln Gly
1

<210> SEQ ID NO 75
<211> LENGTH: 4
<212> TYPE: PRT
<213> ORGANISM: Artificial sequence
<220> FEATURE:
<223> OTHER INFORMATION: VZV N' derived peptide sequence

<400> SEQUENCE: 75

Ile Thr Asn Pro
1

<210> SEQ ID NO 76
<211> LENGTH: 4
<212> TYPE: PRT
<213> ORGANISM: Artificial sequence
<220> FEATURE:
<223> OTHER INFORMATION: Amyliod beta N' derived peptide sequence

<400> SEQUENCE: 76

Asp Ala Glu Phe
1

<210> SEQ ID NO 77
<211> LENGTH: 6
<212> TYPE: PRT
<213> ORGANISM: Artificial sequence
<220> FEATURE:
<223> OTHER INFORMATION: A flexible peptide moiety

<400> SEQUENCE: 77

Gly Ser Gly Gly Ser Ser
1               5

<210> SEQ ID NO 78
<211> LENGTH: 21
<212> TYPE: PRT
<213> ORGANISM: Artificial sequence
<220> FEATURE:
<223> OTHER INFORMATION: MOG35-55 peptide

<400> SEQUENCE: 78

Met Glu Val Gly Trp Tyr Arg Ser Pro Phe Ser Arg Val Val His Leu
1               5                   10                  15

Tyr Arg Asn Gly Lys
            20
```

```
<210> SEQ ID NO 79
<211> LENGTH: 9
<212> TYPE: PRT
<213> ORGANISM: Artificial sequence
<220> FEATURE:
<223> OTHER INFORMATION: Insulysin (IDE) FRET substrate
<220> FEATURE:
<221> NAME/KEY: misc_feature
<223> OTHER INFORMATION: N' Mca conjugated peptide
<220> FEATURE:
<221> NAME/KEY: misc_feature
<223> OTHER INFORMATION: C'  EDDnp conjugated peptide

<400> SEQUENCE: 79

Gly Gly Phe Leu Arg Lys His Gly Gln
1               5

<210> SEQ ID NO 80
<211> LENGTH: 7
<212> TYPE: PRT
<213> ORGANISM: Artificial sequence
<220> FEATURE:
<223> OTHER INFORMATION: TAT cell penetrating peptide

<400> SEQUENCE: 80

Tyr Gly Arg Lys Lys Arg Arg
1               5

<210> SEQ ID NO 81
<211> LENGTH: 11
<212> TYPE: PRT
<213> ORGANISM: Artificial sequence
<220> FEATURE:
<223> OTHER INFORMATION: TAT cell penetrating peptide

<400> SEQUENCE: 81

Tyr Gly Arg Lys Lys Arg Arg Gln Arg Arg
1               5                   10

<210> SEQ ID NO 82
<211> LENGTH: 5
<212> TYPE: PRT
<213> ORGANISM: Artificial sequence
<220> FEATURE:
<223> OTHER INFORMATION: PTD cell penetrating peptide

<400> SEQUENCE: 82

Arg Arg Gln Arg Arg
1               5
```